United States Patent [19]

Mandell et al.

[11] Patent Number: 5,272,153
[45] Date of Patent: * Dec. 21, 1993

[54] METHOD OF INHIBITING THE ACTIVITY OF LEUKOCYTE DERIVED CYTOKINES

[75] Inventors: Gerald L. Mandell, Earlysville; Gail W. Sullivan, Charlottesville, both of Va.; William J. Novick, Lebanon, N.J.

[73] Assignees: Hoechst-Roussel Pharmaceuticals, Inc., Somerville, N.J.; University of Virginia Alumni Patents Foundation, Charlottesville, Va.

[*] Notice: The portion of the term of this patent subsequent to Jun. 15, 2008 has been disclaimed.

[21] Appl. No.: 908,929

[22] Filed: Jul. 2, 1992

Related U.S. Application Data

[63] Continuation of Ser. No. 700,522, May 15, 1991, abandoned, which is a continuation of Ser. No. 622,138, Dec. 5, 1990, Pat. No. 5,096,906, which is a continuation of Ser. No. 508,535, Apr. 11, 1990, abandoned, which is a continuation of Ser. No. 239,761, Sep. 2, 1988, abandoned, which is a continuation of Ser. No. 947,905, Dec. 31, 1986, abandoned, and a continuation of Ser. No. 131,785, Dec. 11, 1987, Pat. No. 4,965,271.

[51] Int. Cl.$^5$ ............................................. A61K 31/52
[52] U.S. Cl. ...................................... 514/263; 514/929
[58] Field of Search ................................ 514/263, 929

[56] References Cited

U.S. PATENT DOCUMENTS

| | | | |
|---|---|---|---|
| 4,558,051 | 12/1985 | Sunshine et al. | 514/261 |
| 4,880,791 | 11/1989 | Weithmann et al. | 514/261 |
| 4,965,271 | 10/1990 | Mandell et al. | 514/929 |
| 4,975,432 | 12/1990 | Weithmann et al. | 514/261 |

FOREIGN PATENT DOCUMENTS

| | | |
|---|---|---|
| 0195496 | 9/1986 | European Pat. Off. . |
| 0267676 | 5/1988 | European Pat. Off. . |
| 0344586 | 5/1988 | European Pat. Off. . |
| 0279079 | 8/1988 | European Pat. Off. . |

OTHER PUBLICATIONS

Avido et al., Angiology 35, 407 (1984).
Suguira et al., Japanese Journal of Anesthesiology 32, 435–41, with English translation.

(List continued on next page.)

Primary Examiner—Nathan M. Nutter
Attorney, Agent, or Firm—Finnegan, Henderson, Farabow, Garrett & Dunner

[57] ABSTRACT

A family of compounds effective in inhibiting interleukin-1 (IL-1) activity, tumor necrosis factor (TNF) activity, and the activity of other leukocyte derived cytokines is comprised of 7-(oxoalkyl) 1,3-dialkyl xanthines of the formula

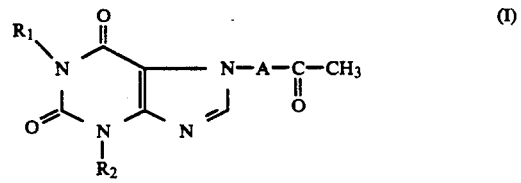

(I)

in which $R_1$ and $R_2$ are the same or different and are selected from the group consisting of straight-chain or branched alkyl radicals with 2 to 6 carbon atoms, cyclohexyl, alkoxyalkyl and hydroxyalkyl radicals, and A represents a hydrocarbon radical with up to 4 carbon atoms which can be substituted by a methyl group. Another family of effective compounds is identified as

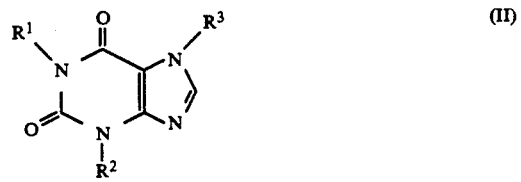

(II)

The inhibition of IL-1, TNF, and other cytokines in mammals is implicated in alleviation of a wide variety of disease conditions.

35 Claims, 6 Drawing Sheets

OTHER PUBLICATIONS

Bessler et al., Journal of Leukocyte Biology, 40:747–54 (1986).

Chemical Abstracts, vol. 104, No. 25, issued Jun. 23, 1986, Abstract No. 218828p.

Chemical Abstracts, vol. 101, No. 19, issued Nov. 5, 1984, Abstract No. 168805u.

John C. Robin et al., Journal of Medicine, vol. 14, No. 2, 1983, Studies on Oesteoporoses.XI–Effects of Methylxanthine Drivative, pp. 137–145.

Clinical Aspects of White Cell Rheology Reference.

METHOD OF INHIBITING THE ACTIVITY OF LEUKOCYTE DERIVED CYTOKINES

CROSS-REFERENCE TO RELATED APPLICATION

This application is a continuation of application Ser. No. 07/700,522 filed May 15, 1991 and now abandoned, which is a continuation of Ser. No. 07/622,138 filed Dec. 5, 1990 and now U.S. Pat. No. 5,096,906, which is a continuation of Ser. No. 07/508,535 filed Apr. 11, 1990 and now abandoned, which is a continuation of Ser. No. 07/239,761 filed Sep. 2, 1988 and now abandoned, which is a continuation of Ser. No. 06/947,905 filed Dec. 31, 1986 and now abandoned, and is a continuation of 07/131,785 filed Dec. 11, 1987 and now U.S. Pat. No. 4,965,271.

BACKGROUND OF THE INVENTION

This invention relates to the inhibition of activity of leukocyte derived cytokines, such as interleukin-1 and tumor necrosis factor, in humans and mammals. More specifically, this invention provides a method of inhibiting the activity of cytokines to arrest or alleviate certain disease and inflammatory states.

Interleukin-1 (IL-1) and tumor necrosis factor (TNF) are biological substances produced by monocytes and other macrophages in mammals. IL-1 and TNF affect a wide variety of cells and tissues, both in vitro and in vivo. Research has demonstrated that IL-1, TNF, and other leukocyte derived cytokines are important, and even critical, mediators in a wide variety of inflammatory states and diseases. The inhibition of IL-1, TNF, and other leukocyte derived cytokines is of benefit in controlling, reducing, and alleviating many of these conditions.

Detection and inhibition of IL-1, TNF, and other leukocyte derived cytokines can be relatively easily documented through in vitro analysis of polymorphonuclear neutrophil behavior. Among other activities attributed to IL-1 and other leukocyte derived cytokines is the promotion of leukocyte adherence and the inhibition of neutrophil chemotaxis, both directly contributing to disease and inflammation syndromes.

Despite the desirability of inhibiting the activity of IL-1 and TNF and the activity of other leukocyte derived cytokines and the ease with which inhibition can be detected in vitro, there exists a need in the art for inhibitors of IL-1, TNF, and other cytokines, wherein the inhibitors are acceptable for in vivo administration.

SUMMARY OF THE INVENTION

This invention aids in fulfilling these needs in the art by identifying a class of compounds that can be successfully employed in alleviating conditions caused by, or mediated by, IL-1, TNF, and other leukocyte derived cytokines. The compounds exhibit marked inhibition of cytokine activity, even at low concentrations of the mediators as demonstrated through in vitro tests.

More particularly, this invention provides a method of inhibiting the activity of IL-1, TNF, and other leukocyte derived cytokines in a mammal comprising administering thereto at least one 7-(oxoalkyl) 1,3-dialkyl xanthine of the formula (I)

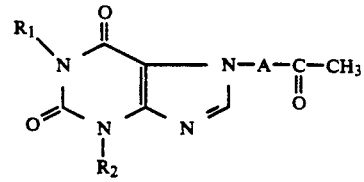

in which $R_1$ and $R_2$ are the same or different and are independently selected from the group consisting of straight-chain or branched-chain alkyl radicals with 2 to 6 carbon atoms, cyclohexyl, straight chain or branched chain alkoxyalkyl, and hydroxyalkyl radicals; and A is a hydrocarbon radical with up to 4 carbon atoms which can be substituted by a methyl group; or a compound of the formula (II)

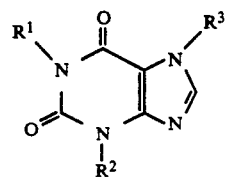

wherein at least one of $R^1$ and $R^3$ is either (a) a branched hydroxyalkyl group of the formula

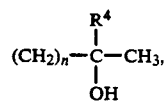

with a tertiary alcohol function, in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or (b) at least one of $R^1$ or $R^3$ is an oxoallyl group of the formula

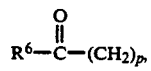

wherein $R^6$ is $C_1$-$C_6$ alkyl, and p=2, 3 or 4. The other $R^1$ or $R^3$ being defined as above; and $R^2$ represents an alkyl group with 1 to 4 carbon atoms. The xanthine of formula (I) or formula (II) is employed in an amount that is effective in inhibiting the activity of IL-1, TNF, and other leukocyte derived cytokines in the mammal.

Exemplary within the general formula (II), and established as an effective IL-1 inhibitor, is the well known and commercially available pharmaceutical pentoxifylline. Although this compound has been used for some time as a pharmaceutical (clinical trials in 1971) it has not been reported effective as an IL-1 inhibitor. It has been demonstrated in promoting directed migration of leukocytes.

BRIEF DESCRIPTION OF THE DRAWINGS

This invention will be more fully described with reference to the drawings in which.

DESCRIPTION OF THE PREFERRED EMBODIMENTS

Figure 1:
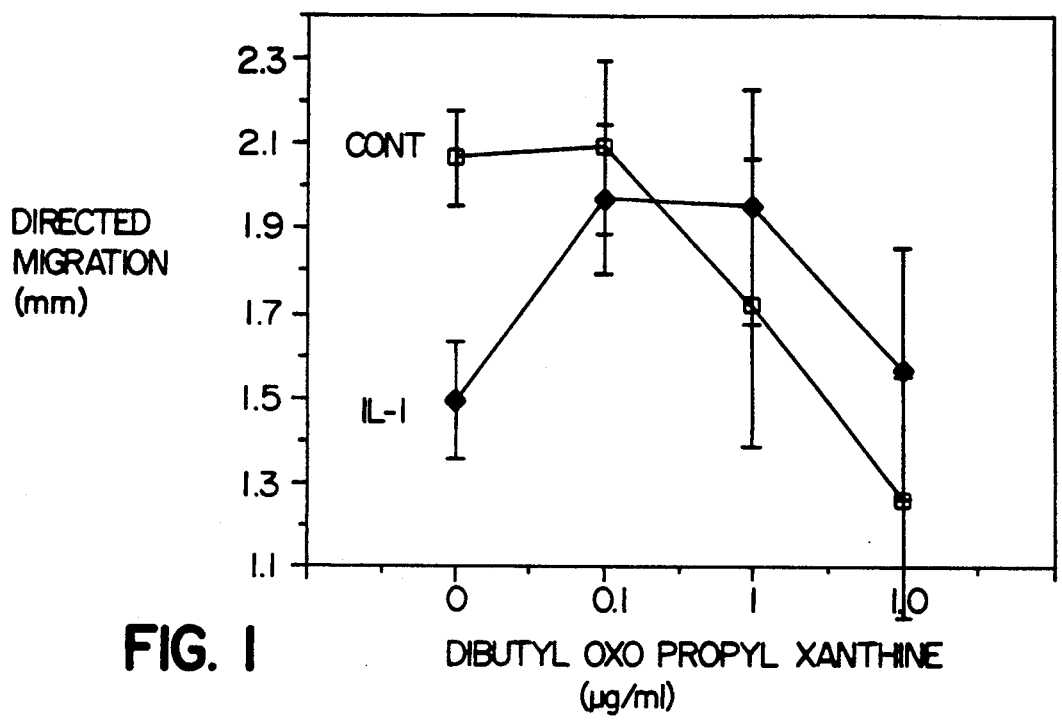
FIG. 1 is a graph showing modulation by 1,3-dibutyl 7-(2-oxopropyl) xanthine (DBOPX) of the effect of interleukin-1 (IL-1) on polymorphonuclear leukocyte (PMN) directed migration to n-formyl methionyl leucyl phenylalanine (FMLP)

Inhibition of the activity of IL-1, TNF, and other leukocyte derived cytokines can be achieved by the administration of xanthines of formula (I) or formula (II) to a mammal.

As used herein, the expression "leukocyte derived cytokines" is to be given a broad meaning. Specifically, the term "leukocyte" as used herein means mammalian cells of granulocytic and lymphocytic lineage. Examples of leukocyte cells are polymorphonuclear leukocytes, such as neutrophils, and mononuclear phagocytes, such as monocytes and macrophages, and lymphocytes.

The term "cytokine" as used herein means a secretory product of a leukocyte, and in particular a non-antibody protein released by a leukocyte on contact with antigen and which acts as an intercellular mediator of immune response. Examples of cytokines that are within the scope of this invention are chemotactic factors, factors promoting replication of lymphocytes, factors inhibiting replication of lymphocytes, factors affecting macrophage adherence, factors affecting enzyme secretion by macrophages, and factors that mediate secretion of oxidizing agents, such as oxygen, superoxide, hydrogen peroxide, and hydroxyl radical.

Xanthines employed in this invention have the following formula:

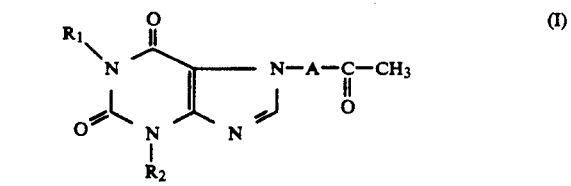

The substituents $R_1$ and $R_2$ in formula (I) are the same or different and are independently selected from the group consisting of straight-chain or branched alkyl radicals with 2 to 6 carbon atoms, cyclohexyl, alkoxyalkyl and hydroxyalkyl radicals. The substituent A represents a hydrocarbon radical with up to 4 carbon atoms, which can be substituted by a methyl group.

A compound that has been found to be particularly effective for inhibiting the effects of IL-1 and other leukocyte derived cytokines on polymorphonuclear leukocytes and monocytes is 1,3-dibutyl 7-(2-oxopropyl) xanthine. This compound, which is also referred to herein in abbreviated form as "DBOPX", has the following formula:

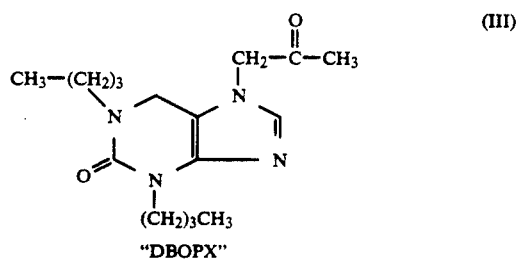

"DBOPX"

The ability of compound (III) to inhibit the effects of IL-1 and other leukocyte derived cytokines on polymorphonuclear leukocyte and monocyte adherence, cell chemotaxis, respiratory (metabolic) burst, and cell degranulation has been demonstrated and is described hereinafter.

Inhibition of IL-1 activity can also be achieved by the administration of compounds of the formula (II)

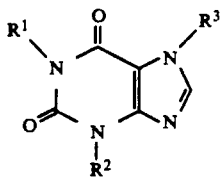

to the host or patient to be treated. As noted, among these compounds is the commercially available pentoxifylline. A host of other compounds within the general formula (II) have been identified as demonstrating IL-1 inhibiting activity. Among these compounds are those identified by their R substituents set forth below.

| Compound # | COMPOUND OF FORMULA (II) | | |
|---|---|---|---|
| | $R_1$ | $R_2$ | $R_3$ |
| 2 | $CH_3-\overset{O}{\underset{\|}{C}}-(CH_2)_4-$ | $-CH_3$ | $-CH_2-CH_2-CH_3$ |
| 3 | $CH_3-\underset{\underset{CH_3}{\|}}{\overset{\overset{OH}{\|}}{C}}-(CH_2)_4-$ | $-CH_3$ | $-CH_2-CH_2-O-CH_3$ |
| 4 | " | " | $-CH_2-O-(CH_2)_2-O-CH$ |
| 5 | " | " | $-H$ |
| 6 | " | " | $-CH_2-CH_2-CH_3$ |
| 7 | " | " | $-CH_2-\overset{\overset{OH}{\|}}{CH}-CH_3$ |
| 8 | " | " | $-CH_2-\overset{\overset{OH}{\|}}{CH}-(CH_3)_2$ |
| 9 | " | $-CH_2-CH_3$ | $-CH_2-O-CH_2-CH_3$ |
| 10 | " | $-CH_3$ | $-(CH_2)_4-\underset{\underset{OH}{\|}}{\overset{\overset{CH_3}{\|}}{C}}-CH_3$ |
| 11 | " | " | $-CH_2-O-CH_2-CH_3$ |

When introduced into polymorphonuclear neutrophil (PMN) incubations provided with IL-1, or incubated in lipopolysaccharide stimulated mononuclear leukocyte condition medium, the compounds of formula (II) of the claimed invention decreased PMN adherence, even at relatively low concentrations (0.1 of micrograms/ml).

Similarly, the presence of the compounds of formula (II) of the claimed invention promoted directed migration of PMN, which migration is inhibited by the presence of IL-1. The demonstrated inhibition of IL-1 by these compounds is, of course, suggestive of clinical effectiveness in the above-identified areas, and additional conditions. Appropriate dosages will vary with the condition and individual.

Phagocytes important in immunology are polymorphonuclear leukocytes (e.g. neutrophils) and mononuclear phagocytes (e.g. monocytes and macrophages). Phagocyte hypofunction is a cause of recurrent pyogenic infection. To combat pyogenic infection, neutrophils and monocytes respond to chemotactic factors by moving toward the source of infection, where they ingest microorganisms and kill them.

More particularly, a main function of polymorphonuclear leukocytes and monocytes is to kill bacteria and other infectious agents by phagocytosis. The first stage in the ingestion and digestion of a particulate substance by these cells involves the process of bringing the cells and the particles together, usually through chemotaxis. This response is an essential part of host defence against infection. The extensive migration and activity of these cells is manifested by inflammation at the site of injury or invasion of the host.

It has been shown that IL-1 and TNF inhibit chemotaxis by granulocytes, monocytes and macrophages. It has now been discovered that the 7-(oxoalkyl)1,3-dialkyl xanthines of formula (I) are capable of modulating the inhibitory effect of IL-1 and TNF on chemotaxis. This has been demonstrated as follows.

The migration of polymorphonuclear leukocytes in response to n-formyl methionyl leucyl phenylalanine (FMLP), a well known chemotactic factor, was determined by chemotaxis under agarose, a well known assay for cell chemotaxis. See J. of Immunol., 115, 6, 1650–1656 (1975). The assay was carried out without IL-1, and the assay was repeated in the presence of IL-1. The assay was also carried out with IL-1, but without DBOPX, and with both IL-1 and DBOPX at DBOPX concentrations of 0.1, 1, and 10 micrograms per milliliter (µg/ml). The results are depicted in FIG. 1.

As shown in FIG. 1, directed migration of the cells in the absence of IL-1, TNF, and with 0 µg/ml DBOPX (i.e. "CONT" in FIG. 1) was about 2.08 mm. Directed migration of the cells dropped to about 1.5 mm in the presence of IL-1, TNF, and with 0 µg/ml DBOPX. Thus, IL-1 inhibited cell chemotaxis directed to FMLP.

FIG. 1 also shows the effect of increasing concentrations of DBOPX on the inhibition of chemotaxis by IL-1. More particularly, DBOPX modulates the inhibitory effect of IL-1 on directed migration to FMLP. Specifically, FIG. 1 shows that DBOPX increased directed migration of the cells and modulated the inhibitory effect of IL-1 at all of the DBOPX concentrations that were evaluated. FIG. 1 also shows that DBOPX was effective in increasing chemotaxis even at very low DBOPX concentrations. Thus, the compounds employed in the process of this invention are particularly effective in modulating the inhibitory effect of IL-1 on cell chemotaxis.

DBOPX is capable of producing a similar effect on polymorphonuclear leukocytes incubated with the products of mononuclear leukocytes that were stimulated with lipopolysaccharide (LPS). These mononuclear cells produce IL-1, TNF, and other inflammatory cytokines. Once again, polymorphonuclear leukocyte directed migration to FMLP was determined by chemotaxis under agarose. The assay was carried out without DBOPX and with concentrations of DBOPX of 0.1, 1.0, 10, and 100 μg/ml. The results are shown in FIG. 2.

Figure 2:
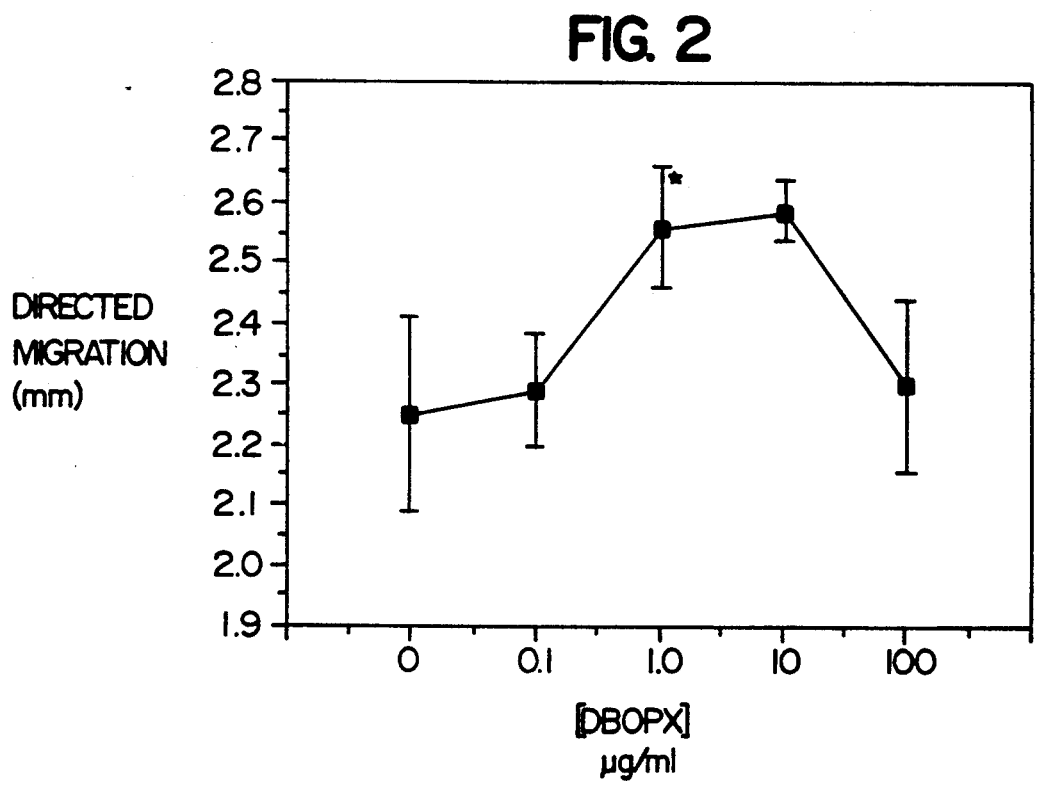
FIG. 2 shows the results of modulation by DBPOX of the effect of mononuclear leukocytes LPS stimulated conditioned medium on PMN directed migration to FMLP.

Referring to FIG. 2, the directed migration of the PMN in the conditioned medium containing the inflammatory cultures was about 2.25 mm in the absence of DBOPX. The addition of DBOPX to the medium increased directed migration of the cells at all of the DBOPX concentrations tested. Once again, DBOPX was effective in increasing chemotaxis even at very low concentrations. Moreover, the directed migration was about 2.6 mm at a DBOPX concentration of 10 μg/ml. By comparison, migration in an unconditioned medium containing LPS was 2.60±0.5 mm. (Data not shown in FIG. 2). The probability that DBOPX increased directed migration inhibited by conditioned medium containing inflammatory cultures was 95%.

DBOPX is capable of producing a similar effect on PMN incubated with rh-TNF (alpha). PMN directed migration to FMLP was determined by chemotaxis under agarose. The assay was carried out without DBOPX and with concentrations of DBOPX of 0.01 mM (3.2 μg/ml) and 1 mM (320 μg/ml). The results are shown in FIG. 3.

Figure 3:
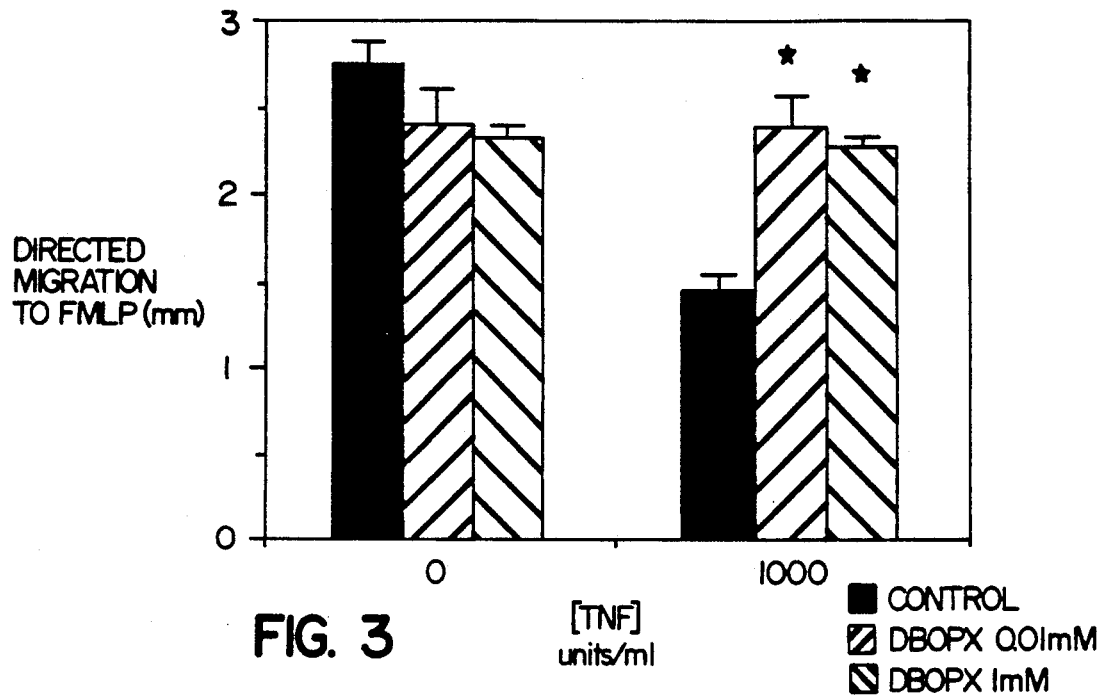
FIG. 3 shows the results of modulation by DBOPX of the effect of tumor necrosis factor (TNF) on PMN directed migration to FMLP.

Referring to FIG. 3, the directed migration of the PMN in medium containing rh-TNF was 1.45 mm in the absence of DBOPX. The addition of DBOPX to the medium increased directed migration of the cells at both of the DBOPX concentrations tested. Once again, DBOPX was effective in increasing chemotaxis even at very low concentrations. By comparison, migration in medium in the absence of TNF was 2.75 mm. The probability that DBOPX increased directed migration inhibited by TNF was better than 95%.

Thus, the 7-(oxoalkyl) 1,3-dialkyl xanthines employed in the process of invention are capable of increasing directional movement of polymorphonuclear leukocytes. These compounds can be administered to a patient to augment chemotactic factors of bacterial or viral origin, or components of plasma activation systems, or factors elaborated by cells of the immune system.

Leukocyte response to an acute inflammatory stimulus involves a complex series of events, including adherence to endothelium near the stimulus. Inhibition of leukocyte adherence can be expected to reduce the degree of inflammation seen in conditions, such a septic shock and adult respiratory distress syndrome. It has been found that the 7-(oxoalkyl) 1,3-dialkyl xanthines employed in this invention effectively block adherence of polymorphonuclear leukocytes.

Specifically, polymorphonuclear leukocyte (PMN) adherence to nylon was determined according to the method of MacGregor et al., New Engl. J. Med. 13:642-646 (1974). Purified PMN cells were incubated with a lipopolysaccharide-stimulated mononuclear leukocyte conditioned medium containing inflammatory cytokines. PMN adherence to nylon was determined without DBOPX, and then with DBOPX at concentrations of 0.1, 1.0, and 10 μg/ml. The percent PMN adherence to nylon was determined for each case. The results are summarized in FIG. 4.

Figure 4:
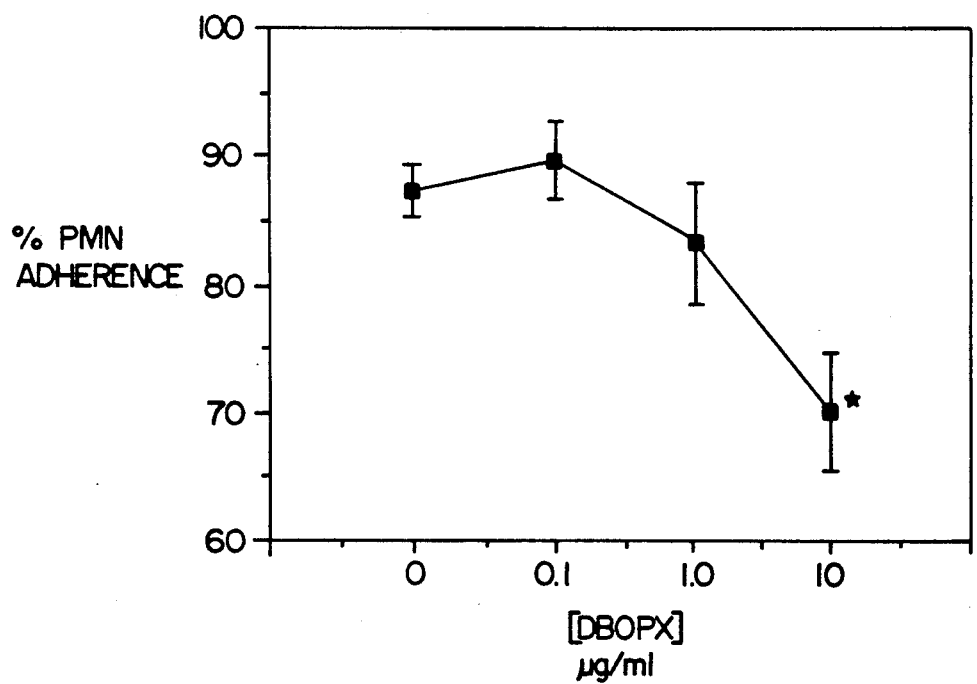
FIG. 4 shows the results of modulation by DBOPX of LPS stimulated mononuclear leukocyte conditioned medium on PMN adherence to nylon.

FIG. 4 shows that PMN adherence to nylon in the absence of DBOPX was about 87%. However, when DBOPX was included in the assay at concentrations above about 0.1 (μg/ml) PMN adherence to the nylon was inhibited as evidenced by a decline in percent adherence. At a DBOPX concentration of 10 (μg/ml) the percent PMN adherence declined to about 70%. The probability that DBOPX decreased adherence of PMN incubated with conditioned medium was 99.7%. Thus, the compounds employed in the process of this invention are particularly effective in blocking adherence of leukocytes and thereby aiding in reducing the degree of inflammation.

Mature phagocytes are in a metabolically dormant state. It is currently believed that recognition of certain objects and substances by phagocytes, such as the attachment of an ingestible particle to the cell surface, changes this situation, and the cell enters a stage of increased metabolic activity, which is referred to as metabolic or respiratory burst. The transition is associated with a series of characteristic changes, including the production of a superoxide anion. Cytokines, such as IL-1 and TNF, are capable of producing a similar effect. In addition to its significance for phagocytic function related to inactivation of ingested microbes, activation of oxygen metabolism is a useful indirect marker for the ingestion process per se. It would be desirable to be able to modulate the effect of cytokines on respiratory burst.

Quantitative methods for direct measurement of hydrogen peroxide and superoxide anions released into the medium are currently available. It has been found that the compounds employed in this invention are capable of modulating respiratory burst in stimulated polymorphonuclear leukocytes (PMN) as determined using these methods.

More particularly, superoxide production was assayed using a modification of the procedure described by Babior et al., J. Clin. Investigation, 52:741-744 (1973). Purified PMN were incubated with an oxidative stimulus with and without IL-1. The medium was assayed for superoxide production. The assay was also carried out without DBOPX and with DBOPX in concentrations of 0.1, 1.0, 10, and 100 μg/ml. The results are shown in FIG. 5.

Figure 5:
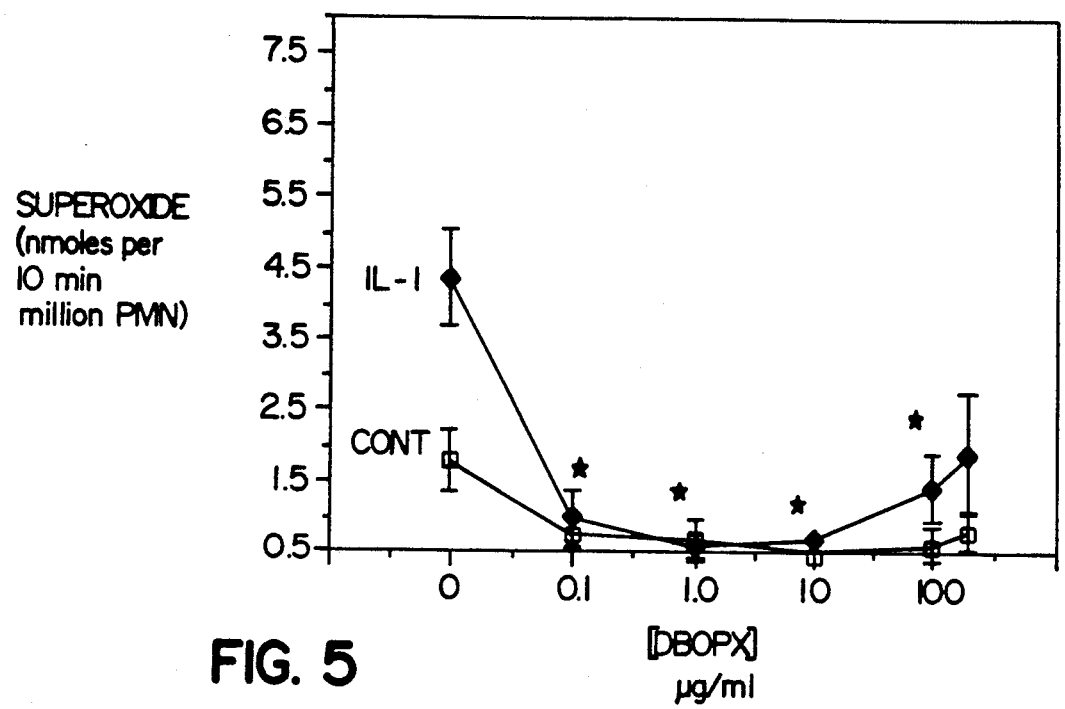
FIG. 5 shows the results of modulation by DBOPX of IL-1 on PMN superoxide release stimulated by FMLP.

It is evident from FIG. 5 that about 1.8 nmoles of superoxide/10 min/million PMN were produced by FMLP-stimulated PMN in the absence of IL-1, TNF, and DBOPX (see "CONT" in FIG. 5). Pretreatment with IL-1 (5 units/20 μl), which is known as priming, produced a substantial increase in observed superoxide release to about 4.4 nmoles superoxide/10 min/million PMN.

In contrast, the addition of DBOPX to the assay resulted in a substantial reduction in observed superoxide production as is evident from FIG. 5. Specifically, DBOPX modulated the effect of IL-1 on stimulated PMN at all of the concentrations tested. DBOPX was even effective at a very low concentration of 0.1 μg/ml. The probability that DBOPX decreased superoxide production produced by PMN primed with IL-1, TNF, and stimulated with FMLP compared with IL-1 alone was 95%.

Figure 6:
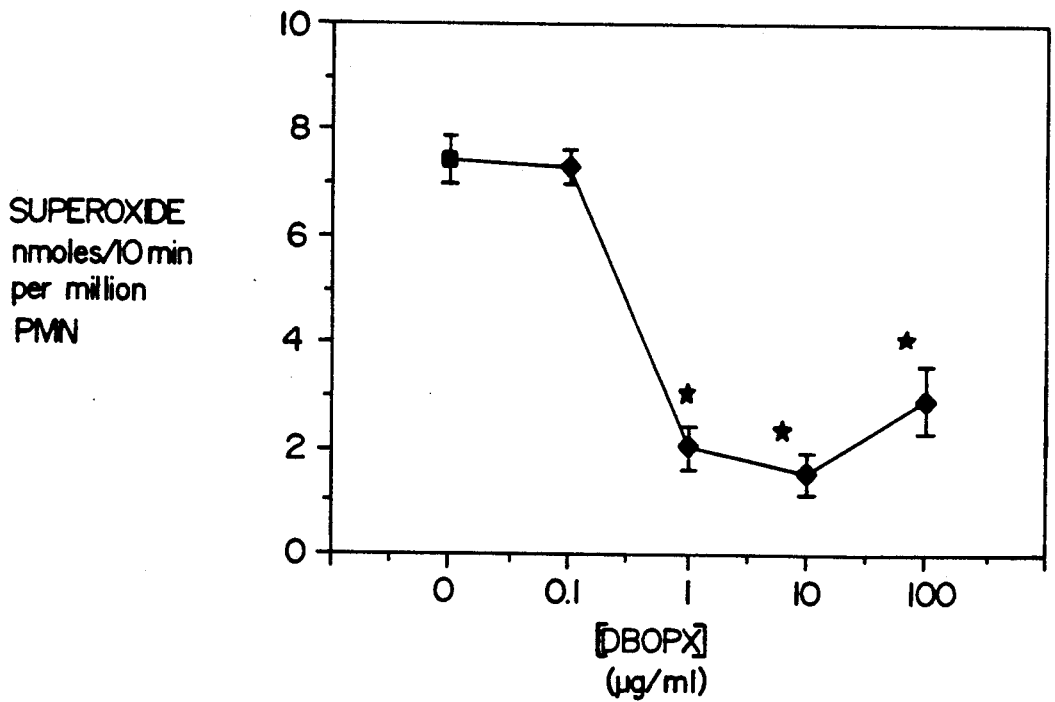
FIG. 6 is a graph showing modulation by DBOPX of lipopolysaccharide (LPS) stimulated mononuclear leukocyte conditioned medium on superoxide production by PMN stimulated with FMLP.

DBOPX is also capable of decreasing superoxide production by PMN primed with LPS-stimulated mononuclear leukocyte conditioned medium containing inflammatory cytokines. This is shown in FIG. 6. Specifically, when PMN were incubated with LPS-stimulated mononuclear leukocyte conditioned medium containing inflammatory cytokines and stimulated with FMLP, observed superoxide production in the absence of DBOPX was about 7.4 nmoles/10 min/million PMN. When DBOPX was added to the assay, however, observed superoxide production was lower at all of the DBOPX concentrations tested. Moreover, DBOPX exhibited some effect even at a concentration as low 1.0 μg/ml. At a DBOPX concentration of 10 μg/ml, superoxide production was about 1.5 nmoles/10 min/million PMN. The probability that DBOPX decreased superoxide production produced by PMN primed with conditioned medium and stimulated with FMLP was 99.5%.

It is evident from these results that the compounds employed in the process of this invention are capable of reducing superoxide production and modulating respiratory burst in phagocytes, such as polymorphonuclear leukocytes and monocytes.

During ingestion, granules in the cytoplasm of the cell fuse with the membrane of a vacuole that was formed around the foreign substance. The granules discharge their contents into the vacuole. Some of this material ends up in the medium surrounding the phagocyte. Since the granules disappear during this process, it is called degranulation. The granule contents include hydrolytic enzymes, lysozyme, bactericidal proteins, and, in the neutrophil, myleoperoxidase.

Degranulation can be assessed by measuring the rate of appearance of granule-associated enzymes in the extracellular medium. In the case of polymorphonuclear leukocytes (PMN), degranulation can be assayed by determining release of lysozyme. It was found that the compounds employed in the process of this invention are capable of modulating the release of lysozyme from stimulated PMN.

More particularly, polymorphonuclear leukocytes (PMN) were incubated with LPS-stimulated mononuclear leukocyte conditioned medium containing inflammatory cytokines. The PMN were then stimulated with FMLP, incubated for a period of time, and lysozyme content was determined in cell supernatant using a well known assay. See *J. Bacteriol.*, 58, 731–736 (1949). The PMN were incubated without DBOPX or with DBOPX in a concentration of 0.1, 1, 10, or 100 μg/ml. The results, which are expressed in terms of lysozyme released/10 min/4 million PMN (μg/ml), are shown in FIG. 7.

Figure 7:
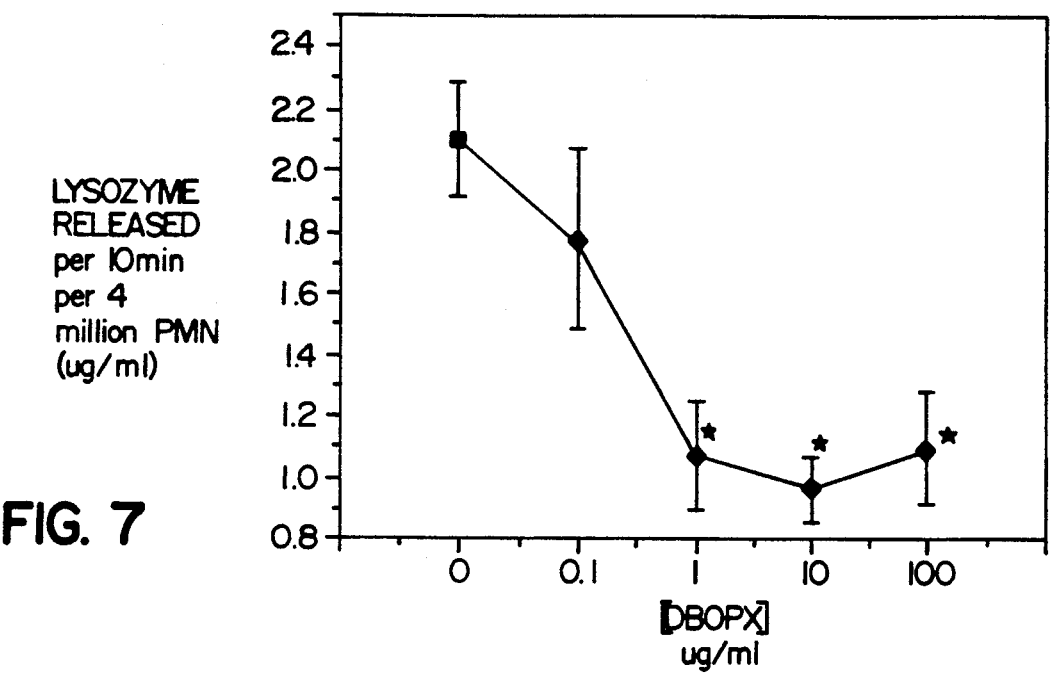
FIG. 7 is a graph showing modulation by DBOPX of the effect of LPS-stimulated mononuclear leukocyte conditioned medium on lysozyme released by PMN stimulated with FMLP.

Referring to FIG. 7, lysozyme released by PMN primed with LPS-stimulated mononuclear leukocyte conditioned medium (containing inflammatory cytokines) and stimulated with FMLP was about 2.1 μg/ml in the absence of DBOPX. When DBOPX was added to the assay, lysozyme release declined. The decrease was observed at all of the concentrations of DBOPX that were evaluated. Moreover, DBOPX was effective in modulating lysozyme release even at concentrations as low as 0.1 μg/ml. At a DBOPX concentration of 100 μg/ml, the lysozyme release was only about 1.04 μg/ml. The probability that DBOPX inhibited lysozyme release from PMN primed with conditioned medium and stimulated with FMLP was 95%.

It is apparent from these results that the compounds employed in the process of this invention are capable of decreasing the release of lysozyme from PMN primed with LPS-stimulated mononuclear leukocyte conditioned medium and then stimulated with FMLP.

In summary, the compounds of formula (I) employed in the process of this invention are capable of modulating the effects of leukocyte derived cytokines, such as interleukin-1 and tumor necrosis factor, on phagocytes, such as polymorphonuclear leukocytes. The compounds are capable of substantially aiding chemotaxis. In addition, the compounds can block adherence of cells. The compounds can decrease oxidative damage to host tissues by phagocytes as evidenced by modulation of respiratory burst in stimulated polymorphonuclear leukocytes. Finally, the compounds can modulate the effects of cytokines on degranulation in stimulated phagocytes. The demonstrated inhibition of IL-1, TNF, and other cytokines by these compounds is suggestive of clinical effectiveness in at least the following areas and conditions.

Because IL-1, TNF, and other leukocyte derived cytokines have been implicated in such a wide variety of mammalian conditions, this invention has a similarly broad scope of application. Among the conditions that can be treated or alleviated by the inhibition of IL-1, TNF, and other leukocyte derived cytokines are: sepsis, septic shock, endotoxic shock, gram negative sepsis, toxic shock syndrome, adult respiratory distress, fever and myalgias due to infection (i.e. influenza), cachexia secondary to infection or malignancy, cachexia secondary to AIDS, rheumatoid arthritis, gouty arthritis, osteoporosis, keloid formation, scar tissue formation, decreased appetite, Crohn's disease, ulcerative colitis, fever due to central nervous system bleeding, glomerulonephritis, multiple sclerosis, Creutzfeld-Jacob disease, adverse reactions to dialysis, diabetes melitus, and psoriasis.

By reference to the specific cause of the disease condition, the more generic term "trauma" can be used. The term "trauma" refers broadly to cellular attack by foreign bodies and physical injury of cells. Included among foreign bodies are microorganisms, particulate matter, chemical agents, and the like. Included among physical injuries are mechanical injuries, such as abrasions, lacerations, contusions, wounds, and the like; therma injuries, such as those resulting from excessive heat or cold; electrical injuries, such as those caused by contact with source of electrical potential; and radiation damage caused, for example, by prolonged, extensive exposure to infrared, ultraviolet or ionizing radiations.

Microorganisms included among the foreign bodies that can elicit a biological response are bacilli, fungi and yeast, viruses, parasites, and the like. Representative bacilli are: Actinomyces spp.; Bacteroides spp.; Corynebacterium spp.; Enterobacteriacea; Enterococcus; Haemophilus spp.; Micrococcus spp.; Neissera spp.; *Staphylococcus aureus; Streptococcus pneumoniae*; Clostridium spp.; *Streptococcus agalactiae*; Bacillus spp.; *H. influenzae*; Moraxella spp.; Mycobacteria spp.; *Pseudodomonas aeruginosa*; Vibrio spp.; and Mycoplasma.

Representative fungi and yeast that are capable of eliciting a biological response are: Microspurum; Blastomcyes; Histoplasma; Aspergillus; Cryptococcus; Candida spp.; Coccidioides; and *Candida albicans*.

Representative viruses are: Rhinovirus; Parainfluenza; Enterovirus; Influenza; Smallpox and vaccinia; Herpes simplex; Measles; Rubella; Arbovirus (Western, Eastern and Venezuelan equine encephalitis, and California encephalitis); Rabies; Colorado tick fever; Yellow fever; Dengue; Hepatitis Virus B (HB Ag); Hepatitis Virus A (HAV); and Human Immunodeficiency Virus (HIV).

Representative parasites that can elicit a response are: *Trypanosoma cruzi; Entamoeba histolytica; Leishmania brasiliensis; Leishmania tropica; Leishmania donovani; Toxiplasma gondii; Plasmodium falcipaum; Trypanosoma rhodesiense; Loa loa; Trichomonas hominis; Schistosoma japonicum; Schistosoma mansoni;* and *Fasciola hepatica*.

Particulate materials capable of eliciting a biological response include silica, asbestos, monosodium urate, cotton fibers coal dust, beryllium, and the like.

Chemical agents include heavy metals, such as lead, chromium, mercury, arsenic, and the like; organic solvents, such as trichloroethylene, and the like; herbicides, such as trichlorophenoxyacetic acid and the like; and pesticides, such as mirex and the like.

In addition, inhibition of IL-1, TNF, and other leukocyte derived cytokines will enhance phagocyte activity in stored blood and blood products.

The compounds employed in this invention will now be described in more detail, and methods for preparing the compounds will be provided.

The process of this invention utilizes 7-(oxoalkyl) 1,3-dialkyl xanthines of formula (I) above. While DBOPX is the particularly preferred xanthine, a number of other compounds can be employed. For example, the xanthines of formula (I) can be substituted by other alkyl groups, or by alkoxy or hydroxyalkyl groups. Suitable alkyl groups include branched and straight chain groups, such as ethyl, propyl, isopropyl, butyl, sec-butyl, tert-butyl, amyl, hexyl, and the like. Alkoxy substituted alkyl groups are branched and straight chain groups containing from 2 to 6 carbon atoms in the combined alkoxy and alkyl groups, including methoxymethyl, amyloxymethyl, methoxyethyl, butoxyethyl, propoxypropyl, and the like. Hydroxyalkyl groups are those containing from 1 to 6 carbon atoms, such as hydroxymethyl, hydroxyethyl, hydroxypropyl, hydroxyhexyl, and the like.

The hydrocarbon groups represented by A in formula (I) above are divalent saturated aliphatic hydrocarbon groups, i.e., methylene, ethylene, trimethylene and tetramethylene, which can be substituted on the carbon adjacent the carbonyl group with methyl. Such methyl-substituted groups include ethylidine, 1,2-propylene, and 1,3-butylene groups.

The compounds of formula (I) employed in this invention can be synthesized using known techniques. For example, the compounds can be prepared at elevated temperature, optionally in the presence of a solvent, by reacting correspondingly substituted 1,3-dialkyl xanthines of the formula

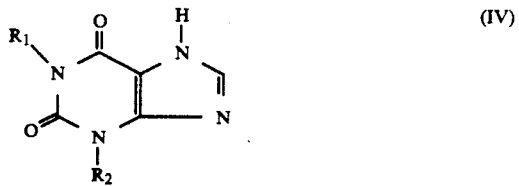

in which $R_1$ and $R_2$ are as defined above, with $\alpha,\beta$-unsaturated methyl ketones corresponding to the formula

The substituent R in formula (V) represents hydrogen or a methyl group. The reaction can be conducted in an alkaline medium.

An alternative method of preparation involves reacting alkali metal salts of 1,3-dialkyl xanthine derivatives of general formula (IV), in which $R_1$ and $R_2$ are as defined above, with oxoalkyl halides corresponding to the formula

in which A is as defined above, and Hal represents a halogen atom, preferably chlorine or bromine.

These reactions are preferably carried out at temperatures in the range from 40° to 80° C., optionally under elevated or reduced pressure, but usually at atmospheric pressure. The individual starting compounds can be employed either in stoichiometric quantities or in excess. The alkali salts in the alternative method of preparation can either be prepared beforehand or in the reaction itself.

Suitable solvents for use in the reactions are water-miscible compounds, preferably lower alcohols, such as methanol, propanol, isopropanol, and various butanols; also acetone; pyridine; triethylamine; polyhydric alcohols, such as ethylene glycol and ethylene glycol monomethyl or monoethyl ether.

The compounds of formula (I) are known for their marked effect in increasing blood flow through skeletal muscle and by their low toxicity. The most active of these compounds for use in accordance with the present invention is 1,3-dibutyl 7-(2-oxopropyl)xanthine, i.e. DBPOX.

A more detailed description of the compounds of formula (I) employed in this invention and methods of preparing the compounds are contained in U.S. Pat. No. 4,242,345, the entire disclosure of which is relied upon and incorporated by reference herein.

As noted, among the compounds of formula (II) embraced in this invention is pentoxifylline (Trental ®). Other compounds can be prepared according to the disclosure of U.S. Pat. No. 3,737,433 and Belgium Patent 831,051 (where $R^1/R^3$ are oxoallyl). For the cases where at least one of $R^1/R^3$ is a tertiary alcohol reference may be had to the international application PCT-EP-86-00401, Jul. 8, 1986 claiming German priority of Jul. 8, 1985. This application addresses, as its invention, a variety of embodiments of synthesis routes for the xanthines of formula (II) embraced in the current invention.

An example of one embodiment consists of
a) reacting 3-alkylxanthines of formula (VII)

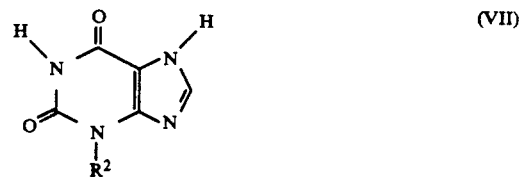

in which the $R^3$ represents alkyl with up to 4 carbon atoms, with alkylating agents of formula (VIII)

in which X stands for halogen, preferably chlorine, bromine, or iodine, or a sulfonic acid ester group or a phosphoric acid ester group and $R^4$ and n have the meanings mentioned above, to obtain compounds of formula (IX)

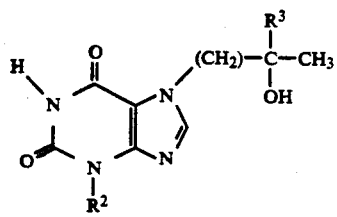 (IX)

with a tertiary hydroxyalkyl group in the position of $R^3$ and hydrogen in the position of $R^1$, and a₁) alkylating this with the same or different alkylating agent of formula (VIII) to obtain compounds pursuant to the invention of formula (X)

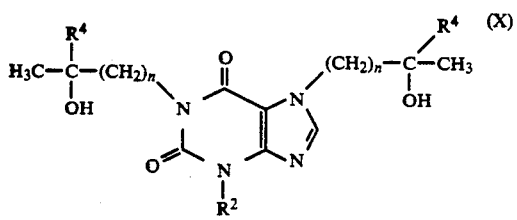 (X)

with two identical or different tertiary hydroxyalkyl groups in the positions of $R^1$ and $R^3$, or a₂) converting it with a compound of the formula $$R^5-X \quad (Xa)$$

in which X has the meaning given in formula (VIII) and $R^5$ has the meaning indicated above, into compounds of formula (XI)

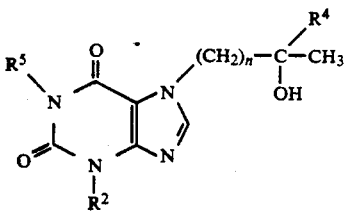 (XI)

in all cases preferably operating in the presence of basic media or using the xanthines in the form of their salts.

Another form of embodiment b) consists of substituting 1,3-dialkylated xanthines of formula (XII)

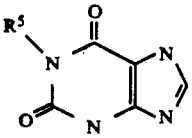 (XII)

in the α-position, preferably in the presence of basic media or in the form of their salts, by one-step reaction with a compound of formula (VIII), to obtain compounds of formula (XI).

Another form of embodiment c) consists of first reacting the 3-alkylxanthines of formula (VII), likewise preferably in the presence of basic media or in the form of their salts, with a compound of the formula $$R^{15}-X \quad (XIII)$$

with the formation of 3,7-disubstituted xanthines of formula (XIV)

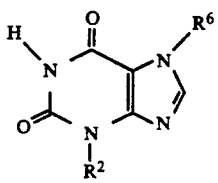 (XIV)

in which $R^{15}$ has the meaning mentioned for $R^5$ or stands for benzyl or diphenylmethyl, and then substituting them in the 1-position, again preferably in the presence of basic media or in the form of their salts, with a compound of formula (VIII), with compounds of formula (XV)

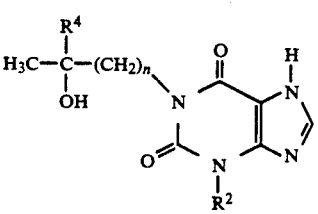 (XV)

being obtained, and converting the compounds of formula (XV) in which $R^{15}$ represents a benzyl or diphenylmethyl being obtained, and converting the compounds of formula (XV) in which $R^{15}$ represents a benzyl or diphenyimethyl group or an alkoxymethyl or alkoxyalkoxymethyl group, under reducing or hydrolytic conditions, into compounds pursuant to the invention of formula (XVI)

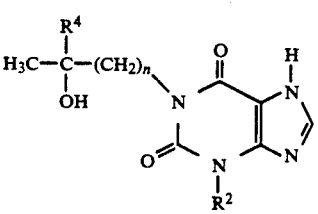 (XVI)

that are subsequently reacted again, if desired, with a compound of formula (VIII) or (Xa) to obtain compounds pursuant to the invention of formula (X) or (XV).

Another form of embodiment d) consists of reducing compounds of formula (XI) or (XV) pursuant to the invention in which $R^5$ or $R^{15}$ stands for an oxoalkyl group, with conventional reducing agents for the keto group to obtain the corresponding hydroxyalkylated xanthines pursuant to the invention.

The 3-alkyl- or 1,3-dialkylxanthines of formula (VII) or (XII) used here as starting materials and the "alkylating agents" of formulas (VIII), (Xa), and (XIII) are known for the most part or can be prepared readily by methods disclosed in the literature. Thus, the tertiary alcohols of formula (VIII), for example, can be obtained by organometallic synthesis by reacting the sterically unhindered haloketones of the formula $$Hal-(CH_2)_n-CO-CH_3 \quad (XVII)$$

in a so-called synthetic reaction with reductive alkylation of the carbonyl group, with alkylmetal compounds $R^4$-M, especially of magnesium, zinc, or lithium, for example in the form of alkylmagnesium halides $R^4$-MgHal (Grignard compounds) or of the alkyllithium compounds $R^4$-Li under the usual conditions (for example, see Houben-Weyl, Vol. VI/1 a, Part 2 (1980), pp. 928-40, especially pp. 1021 ff. and 1104-1112). In the same way, a reaction of the haloketones with the formula

$$\text{Hal}-(CH_2)_n-CO-R^4 \qquad (XVIII)$$

with methylmagnesium halides or methyllithium likewise leads to the target.

The hydroxyketones corresponding to the formulas (XVII) and (XVIII) can also be converted smoothly into diols with the alkylmetal compounds in the usual way, either directly or with temporary masking of the hydroxy group, for example by acetal formation with 5,6-dihydro-4H-pyran (for example, see Houben-Weyl, Vol. VI/1 a, Part 2 (1980), pp. 1113-1124), from which compounds of formula (VIII) are formed by selective esterification of the terminal primary hydroxyl groups with sulfonyl or phosphoric halides or anhydrides, advantageously in the presence of basic media.

Other possibilities for the synthesis of the tertiary alcohol derivatives of formula (VIII) consist of the monometallation of ω-chloro-1-bromoalkanes to obtain ω-chloroalkylmetal compounds, (Houben-Weyl, Vol. XIII/2 a (1973), pp. 102 and 319) and their subsequent reaction with the ketones $R^4$—CO—CH$_3$, with the extent of by-product formation from the alkanolates formed as intermediates because of their tendency toward ring closure with the elimination of metal salt being minimized by appropriate temperature control, or of using ω-halo-1-alkanols as starting materials, which are metallated in the usual way, preferably in the form of the tetrahydropyranyl-(2) ether or after alkanolate formation of the hydroxy group (MO—(CH$_2$)$_n$—Hal) with any desired alkylmetal compound (for example, see Houben-Weyl, Vol. XIII/2 a (1973, p. 113), then reacting them with the ketones $R^4$—CO—CH$_3$ to obtain the diols mentioned in the preceding paragraph (Houben-Weyl, Vol. VI/1 a, Part 2 (1980), p. 1029), and subsequently selectively esterifying the primary hydroxy group with suitable sulfonic or phosphoric acid derivatives.

A convenient access to compounds of formula (VIII) in which $R^4$ represents a methyl group is also available through the reaction of ω-haloalkanoic acid alkyl esters (Hal—(CH$_2$)$_n$—COO—alkyl) with two equivalents of a methylmetal compound, with the ester reacting through the ketone to produce the tertiary alcohol with the introduction of two methyl groups (Houben-Weyl, Vol. VI/1 a, Part 2 (1980), pp. 1171-1174). In the same way, ω-hydroxycarboxylic acid esters can be converted into diols with methylmetal compounds with or without protection of the hydroxy group, for example in the form of tetrahydropyranyl-(2) or methoxymethyl ether, or optionally in the form of the lactones as cyclic esters (for example, see Houben-Weyl, Vol. VI/1 a, part 2 (1980), pp. 1174-1179), from which active alkylating agents of formula (VIII) can in turn be obtained by selective esterification of the primary hydroxyl group with sulfonic or phosphoric halides or anhydrides.

Suitable compounds of formula (VIII) that can be prepared by the methods described above are thus the [(ω-1)-hydroxy-(ω-1)-methyl]butyl, -pentyl, -hexyl, and -heptyl, the [(ω-2)-hydroxy-(ω-2)-methyl]pentyl, -hexyl, -heptyl, and -octyl, and the [(ω-3)-hydroxy-(ω-3)-methyl]hexyl, -heptyl, -octyl, and -nonyl chlorides, bromides, iodides, sulfonates, and phosphates.

Among the compounds of formula $R^5$—X (Xa) or $R^{15}$—X (XIII) suitable for the introduction of $R^5$ into the 1- or 7-position and of $R^{15}$ into the 7-position of the xanthine skeleton, the alkoxymethyl and alkoxyalkoxymethyl derivatives occupy a special position as their halides can indeed be used successfully as reactants but toxicological problems can arise, at least in large-scale use. For this reason, the use of the corresponding sulfonates is preferred in this special case, which are readily available, for example, by reacting mixed anhydrides of aliphatic carboxylic acids and aliphatic or aromatic sulfonic acids (M. H. Karger et al., J. Org. Chem. 36 (1971), pp. 528-531) with the formaldehyde dialkyl acetals or dialkoxyalkyl acetals in a smooth and nearly quantitative reaction (M. H. Karger et al., J. Amer. Chem. Soc. 91 (1969), pp. 5663/5665:

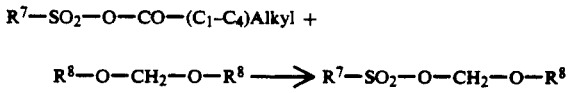

$$R^7-SO_2-O-CO-(C_1-C_4)\text{Alkyl} \ +$$

$$R^8-O-CH_2-O-R^8 \longrightarrow R^7-SO_2-O-CH_2-O-R^8$$

In this equation, $R^7$ represents an aliphatic group such as methyl, ethyl, or trifluoromethyl, or an aromatic group, for example, phenyl, 4-tolyl, or 4-bromophenyl, but preferably methyl or 4-tolyl, and $R^8$ represents an alkyl or alkoxyalkyl group falling under the definition of $R^5$ or $R^{15}$.

The reaction can be carried out either in the substance or in an anhydrous aprotic solvent inert to the reactants at temperatures between −20° and +40° C., preferably between 0° and 20° C. No intermediate isolation of the highly reactive sulfonates, which are sensitive to hydrolysis and thermally labile, is necessary; they are preferably used immediately as crude products for the substitution on the nitrogen of the xanthines, with the usual addition of a basic condensing agent being unnecessary.

The reaction of the mono- or disubstituted xanthine derivatives, (IX), (XVI), (VII), (XII), and (XIV) with the alkylating agent involved of formula (VIII) or (Xa) or (XIII) is ordinarily done in a distributing agent or solvent inert to the reactants. Practical representatives are especially dipolar, aprotic solvents, for example formamide, dimethylformamide, dimethylacetamide, N-methylpyrrolidone, tetramethylurea, hexamethylphosphoric triamide, dimethyl sulfoxide, acetone, or butanone; however, alcohols such as methanol, ethylene glycol, and their mono- or dialkyl ethers with the alkyl group having 1 to 4 carbon atoms but both together having a maximum of 5 carbon atoms, ethanol, propanol, isopropanol, and the various butanols; hydrocarbons such as benzene, toluene, or xylenes; halogenated hydrocarbons such as dichloromethane or chloroform; pyridine, and mixtures of the solvents mentioned or their mixtures with water can also be used.

The "alkylation reactions" are suitably carried out in the presence of a basic condensing agent. Examples of materials suitable for this are alkali metal or alkaline earth hydroxides, carbonates, hydrides, alcoholates, and organic bases, such as trialkylamines (for example, triethyl- or tributylamine), quaternary ammonium or phosphonium hydroxides and crosslinked resins with fixed, optionally substituted ammonium or phosphonium groups. The xanthine derivatives can also be used in the alkylation reaction directly in the form of their separately prepared salts, such as the alkali metal, alkaline earth, or optionally substituted ammonium or phosphonium salts. The mono- and disubstituted xanthine derivatives can also be alkylated either in the presence of the aforementioned inorganic condensing agents or in the form of their alkali metal or alkaline earth salts with the assistance of so-called phase transfer catalysts, for example tertiary amines, quaternary ammonium or phosphonium salts. or crown ethers, preferably in a 2-phase system under the conditions of phase transfer catalysis. Among the suitable phase transfer catalysts that are generally commercially available are tetra($C_1$–$C_4$)alkyl- and methyltrimethylammonium and -phosphonium salts, methyl-, myristyl-, phenyl-, and benzyltri ($C_1$–$C_4$)alkyl- and cetyltrimethylammonium as well as ($C_1$–$C_{12}$)alkyl- and benzyltriphenylphosphonium salts, with the compounds that have the larger and more symmetrically structured cation generally proving to be the more effective.

The introduction of the groups Ia, $R^5$, and $R^{15}$ by the procedures described above is generally carried out at a reaction temperature between 0° C. and the boiling point of the particular reaction medium used, preferably between 20° and 130°, optionally at elevated or reduced pressure, for which the reaction time can amount to less than 1 hour or up to several hours.

The reaction of the 3-alkylxanthines (VIII) to produce the compounds pursuant to the invention of formula (X) requires the introduction of two tertiary hydroxyalkyl groups. Either identical or different substituents can be linked to the xanthine skeleton in succession, or two identical hydroxyalkyl groups can be linked without isolation of intermediates in a single-pot reaction.

The reductive cleavage of the benzyl and diphenylmethyl group from compounds of formula (XV) with the formation of the xanthine atom in the 7-position, is carried out under standard conditions that were developed especially in the framework of the protective group technique in alkaloid and peptide syntheses and can thus be assumed to be widely known. Besides the chemical reduction, particularly of the benzyl compounds with sodium in liquid ammonia (Houben-Weyl, Vol. XI/1 (1957), pp. 974–975), the elimination of the two aforementioned aralkyl groups by catalytic hydrogenolysis using a precious metal catalyst is also especially practical (Houben-Weyl, Vol. XI/1 (1957), pp. 968–971 and Vol. IV/l c, Part I (1980), pp. 400–404). A lower alcohol is ordinarily used here as the reaction medium (optionally with the addition of formic acid or ammonia), or an aprotic solvent such as dimethylformamide or particularly glacial acetic acid; however, their mixtures with water can also be used. Especially suitable hydrogenation catalysts are palladium black and palladium on activated charcoal or barium sulfate, while other precious metals such as platinum, rhodium, and ruthenium frequently given rise to side reactions because of competitive ring hydrogenation and are therefore only conditionally usable. The hydrogenolysis is preferably carried out at temperatures between 20° C. and 100° C. and at atmospheric pressure, or preferably slight excess pressure up to approximately 10 bar, with reaction times of a few minutes to several hours generally being needed.

The 1,3,7-trisubstituted xanthines of formula (XV) that have an alkoxymethyl or alkoxyalkoxymethyl group in the position of $R^{15}$ represent O,N-acetals. Consequently, their substituents in the 7-position can be split off under the usual conditions of acid hydrolysis (cf. Houben-Weyl, Vol. VI/I b (1984), pp. 741–745), with the 7H compounds of formula (XVI) likewise being formed. Examples of preferred groups that can be eliminated hydrolytically are the methoxy, ethoxy, and propoxymethyl groups as well as the methoxyethoxy- and ethoxyethoxymethyl groups. The reaction is advantageously carried out with heating in dilute mineral acids such as hydrochloric or sulfuric acid, optionally with the addition of glacial acetic acid, dioxane, tetrahydrofuran, or a lower alcohol as a solution promoter. Also useful are perchloric acid or organic acids such as trifloroacetic, formic, and acetic acid, in combination with catalytic amounts of mineral acids. The alkoxyalkoxymethyl compounds in particular can also be cleaved by using Lewis acids such as zinc bromide and titanium tetrachloride in anhydrous medium, preferably in dichloromethane or chloroform, with the 7-bromomethyl or 7-bromozinc derivatives formed as intermediates hydrolyzing spontaneously during the aqueous workup. In the cleavage in mineral acid solution, the reaction temperature must be chosen so that no significant dehydration of the tertiary hydroxyalkyl group in the 1-position occurs; it should therefore be below 100° C. as a rule.

The reduction of the xanthines of formulas (XI) and (XV) with an oxoalkyl group in the position of $R^5$ or $R^{15}$ to the corresponding hydroxyalkyl compounds can indeed take place in principle either with base metals or by catalytic hydrogenation, but the method of choice consists of the reaction occurring under the very mild conditions and in high yields with simple metal hydrides ($MH_n$), complex metal hydrides ($M^1[M^2H_n]_m$), or organometallic hydrides (Houben-Weyl, Vol. IV/1 d (1981), pp. 267–282, and Vol. VI/1 b (1984), pp. 141–155). Of the numerous complex metal hydrides that can be used for the reduction of ketones, the most frequently used reagents might be mentioned, for example, lithium alanate, lithium borohydride, and especially sodium borohydride, that is easier to handle because of its lower reactivity and above all permits working in alcoholic, alcoholic aqueous, and pure aqueous solutions or suspensions. In addition to the otherwise customery inert solvents such as ethers (for example, diethyl ether, tetrahydrofuran, 1,2-dimethoxyethane), hydrocarbons and pyridine, nitriles such as acetonitrile can also be used as the reaction medium. The hydrogenation, which is suitably carried out at temperatures between 0° C. and the boiling point of the particular solvent, but preferably at room temperature, generally occurs rapidly and is complete within several minutes to a few hours.

The tertiary hydroxyalkylxanthines of formula (II) can also be prepared by reacting substituted xanthines of formula (XIX)

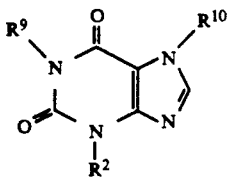 (XIX)

e) contain two identical or different groups of the formula

—(CH$_2$)$_n$—CO—CH$_3$ (XX)

or

—(CH$_2$)—$_n$—CO—R$^4$ (XXI), or only one substituent of the formula (XX) or (XXI), and hydrogen or the group R$^5$ or R$^{15}$ in the positions of R$^9$ and R$^{10}$, with (C$_1$–C$_3$)alkyl- or methylmetal compounds with reductive "alkylation" of the carbonyl groups to obtain the xanthines pursuant to the invention of formulas (IX) to (XVI), or f) metallating xanthines of formula (XIX) that have two identical or different groups of the formula —(CH$_2$)$_n$—Hal (XVII), with Hal preferably standing for chlorine or bromine, or only one such group and hydrogen or the substituent R$^5$ or R$^{15}$ in the other position, in the terminal position, and then reacting them with the ketones of the formula

R$_4$—CO—CH$_3$ (XVIII)

with reductive alkylation of the carbonyl group to obtain the xanthines of formulas (IX) to (XVI) pursuant to the invention, or g) converting xanthines of formula (XIX) with the group

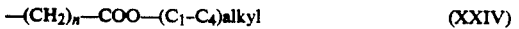
—(CH$_2$)$_n$—COO—(C$_1$–C$_4$)alkyl (XXIV)

in the positions of R$^9$ and/or R$^{10}$ and optionally hydrogen or the group R$^5$ or R$^{15}$ in the other position, by means of two equivalents of a methylmetal compound per alkoxycarbonyl group, into xanthines of formulas (IX) to (XVI) in which R$^4$ stands for methyl, or h) converting xanthines of formula (XIX) having two identical or different groups of the formula

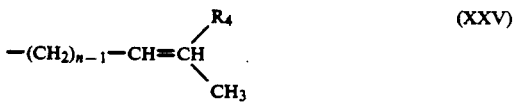
—(CH$_2$)$_{n-1}$—CH=CH(R$_4$)(CH$_3$) (XXV)

or only one such group and hydrogen or the group R$^5$ or R$^{15}$ in the positions of R$^9$ and R$^{10}$, in which the group (XXV) can contain the C=C double bond also in position-isomeric arrangements on the branched carbon atom, for example, as —C=CH$_2$, by acid-catalyzed hydration obeying the Markownikoff Rule, into the xanthines of formulas (IX) to (XVI) pursuant to the invention, and if desired, then converting the tertiary hydroxyalkylxanthines of formulas Ib' and if obtained pursuant to the invention by methods e) to h) that have a hydrogen atom in the 1- or 7-position, optionally in the presence of basic media or in the form of their salts, with the alkylating agents of formula (VIII) or (Xa) or (XIII), into the trisubstituted compounds of formulas (X) or (XI) or (XV), in which R$^2$, R$^4$, R$^5$, R$^{15}$, and n in the formulas above have the meanings indicated above.

The 3-alkylated mono- or dioxoalkyl- (XIXa), -(ω-haloalkyl) (XIXb), -(ω-alkoxycarbonylalkyl)- (XIXc), and -alkenylxanthines (XIXd) needed for this as starting materials are either known or can be prepared readily, for example, from the 3-alkyl-xanthines (VII) and the sulfonyloxy- or haloketones (XVII) and (XVIII), ω-haloalkylsulfonates, or 1, ω-dihaloalkanes (cf., for example: V. B. Kalcheva et al., Journal fur prakt. Chemie 327 (1985) pp. 165–168), ω-sulfonyloxy or ω-halocarboxylic acid alkyl esters or sulfonyloxy or haloalkenes corresponding to formula (XXV) under the reaction conditions previously described in detail for the alkylation of mono- and disubstituted xanthines with the compounds of formulas (VIII) and (Xa)

In the organometallic reactions of the xanthines (XIXa) and (XIXc) functionalized in the R$^9$ and R$^{10}$ groups, the procedure is the same in principle as described for the preparation of the tertiary alcohols of formula (VIII) used as alkylating agents. Thus, the reductive alkylation of the ketones (XIXa) and of the esters (XIXc) can take place, for example, with alkylpotassium, -sodium, -lithium, -magnesium, -zinc, -cadmium, -aluminum, and -tin compounds. The recently recommended alkyltitanium and -zirconium compounds (D. Seebach et al., Agnew, Chem. 95 (1983), pp. 12–26) can also be used. However, since the alkylmetal compounds of sodium and potassium have a tendency toward side reactions because of their high reactivity and those of zinc and cadmium are relatively sluggish, the alkyllithium and -magnesium (Grignard) compounds are ordinarily preferred.

The strong nucleophilic organometallic compounds are very sensitive to hydrolysis and oxidation. Their safe handling therefore requires working in anhydrous medium, optionally under an inert gas atmosphere. The usual solvents or distributing agents are primarily those that are suitable also for the preparation of the alkylmetal compounds. Practical examples are especially ethers with one or more ether oxygen atoms, for example diethyl, dipropyl, dibutyl, or diisoamyl ether, 1,2-dimethoxyethane, tetrahydrofuran, dioxane, tetrahydropyran, furan, and anisole, and aliphatic or aromatic hydrocarbons such as petroleum ether, cyclohexane, benzene, toluene, xylenes, diethylbenzenes, and tetrahydronaphthalene; however, tertiary amines such as triethylamine, or dipolar aprotic solvents such as hexamethylphosphoric triamide, as well as mixtures of the solvents mentioned can also be used successfully. The reaction of the carbonyl compounds (XIXa) and (XIXc) with the Grignard compounds with the formula R$^4$-MgHal can also beneficially be carried out by placing the organometallic compound in an ether and adding the ketone or the ester dropwise as a solution in dichloromethane or 1,2-dichloroethane. An addition of magnesium bromide is frequently recommended, which is able to increase the nucleophilicity of the organometallic compound because of its participation in the complex cyclic transition state.

The ketone or ester and the organometallic compound are generally combined at temperatures between −20° C. and 100° C., preferably between 0° C. and 60°, or at room temperature without external cooling, with the alkylmetal compound ordinarily being used in slight excess. The reaction is then ordinarily completed by brief heating under reflux, for which times of several minutes to a few hours are generally adequate. The alkanolate formed is preferably decomposed with aqueous ammonium chloride solution or dilute acetic acid.

Metallic magnesium and lithium are primarily suitable for the metallation of the ω-haloalkylxanthines (XIXb). On the other hand, the replacement of the halogen atom with lithium, which is also possible using organolithium reagents, generally 1-butyl-, 2-butyl-, t-butyl-, or phenyllithium, plays a subordinate role. However, use is made especially of the Grignard compounds, advantageously preparing them in the ethers, hydrocarbons, tertiary amines, or aprotic solvents listed as particularly suitable for the reaction of the xanthines (XIXa) and (XIXc) with alkylmetal compounds, at temperatures between 25° and 125° C., preferably below 100° C. If the metallation reaction is carried out in hydrocarbons, then the addition of an ether such as tetrahydrofuran, or a tertiary amine such as triethylamine in stoichiometric amount frequently proves useful. The use of catalysts such as butanol, aluminum chloride, silicon tetrachloride, tetrachloromethane, and aluminum or magnesium alcoholates may also be helpful. In the halogen-metal exchange the chlorides ordinarily react more slowly than the corresponding bromides and iodides, but as a rule they provide better yields of organometallic compound. To accelerate the beginning of the reaction, the addition of some magnesium bromide, some grains of iodine, or several drops of bromine, tetrachloromethane, or methyl iodide with slight heating is frequently recommended. The Grignard compounds obtained are normally not isolated, but are reacted immediately with the ketones of formula (XXIII) under the reaction conditions described for the reductive alkylation of the xanthines (XIXa) and (XIXc).

The addition of water to the C=C double bond of the alkenylxanthines (XIXd) with the structural element of formula (XXV), in which the hydroxy group adds to the carbon atom with the fewer hydrogens to form tertiary alcohols according to the Markownikoff Rule, ordinarily occurs in aqueous solution or suspension in the presence of strong acids such as sulfuric, nitric, or phosphoric acid. Hydrogen halides and sulfonic acids such as trifluoromethanesulfonic acid, acid exchange resins, boron trifluoride complexes, or oxalic acid can also be used as catalysts. However, it is preferred to operate in sulfuric acid, with an acid concentration of 50 to 65% and temperatures of 0° to 10° C. being sufficient as a rule. However, lower or higher acid concentration and/or reaction temperatures can sometimes also be used. In any case, the reaction temperatures should be kept as low as possible since the reverse dehydration to the olefin can be disturbingly significant above approximately 60° C.

The addition of a solvent inert to acids such as 1,4-dioxane, benzene, or toluene sometimes also provides benefits. Since esters can form as intermediates in the acid-catalyzed hydration, particularly when using the high acid concentrations, it is recommended to treat the reaction batch with a large amount of water with brief heating after the action of the acid for the purpose of ester hydrolysis, or to process the mixture in the alkaline range.

The experimental conditions for the optional conversion of the 1- and 7H-compounds (IX) or (XVI) pursuant to the invention into the trisubstituted xanthines of formulas (X) or (XI) or (XVI) by N-alkylation with the compounds (VIII) or (Xa) of (XIII) have already been described above in detail.

Depending on the chain length of the alkyl group $R^4$ (at least $C_2$) and/or the structure of a substituent $R^5$ (for example, 2-hydroxypropyl), the tertiary hydroxyalklyxanthines of formula (II) can have one or two asymmetric carbon atoms and can thus be present in stereoisomeric forms. This invention therefore concerns both the pure stereoisomeric compounds and their mixtures.

Effective amounts of the xanthines can be administered to a subject by any one of various methods, for example, orally as in capsule or tablets, or parenterally in the form of sterile solutions. The xanthines, while effective themselves, can be formulated and administered in the form of their pharmaceutically acceptable addition salts for purposes of stability, convenience of crystallization, increased solubility, and the like.

Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as, maleic acid, fumaric acid, oxalic acid, and the like; and salts of tribasic carboxylic acids, such as, carboxysuccinic acid, citric acid, and the like.

The xanthines can be administered orally, for example, with an inert diluent or with an edible carrier. They can be enclosed in gelatin capsules or compressed into tablets. For the purpose of oral therapeutic administration, the compounds can be incorporated with excipients and used in the form of tablets, troches, capsules, elixirs, suspensions, syrups, wafers, chewing gums, and the like. These preparations should contain at least 0.5% of active compound, but the amount can be varied depending upon the particular form and can conveniently be between 4.0% to about 70% of the weight of the unit. The amount of xanthine in such compositions is such that a suitable dosage will be obtained. Preferred compositions and preparations according to the present invention are prepared so that an oral dosage unit form contains between about 1.0 mgs and about 300 mgs of active compound.

Tablets, pills, capsules, troches, and the like can contain the following ingredients: a binder, such as microcrystalline cellulose, gum tragacanth or gelatin; an excipient, such as starch or lactose; a disintegrating agent, such as alginic acid, Primogel, corn starch, and the like; a lubricant, such as magnesium stearate or Sterotes; a glidant, such as colloidal silicon dioxide; a sweetening agent, such as sucrose or saccharin; or flavoring agent, such as peppermint, methyl salicylate, or orange flavoring. When the dosage unit form is a capsule, it can contain, in addition to material of the above type, a liquid carrier, such as a fatty oil.

Other dosage unit forms can contain other materials that modify the physical form of the dosage unit, for example, as coatings. Thus, tablets or pills can be coated with sugar, shellac, or other enteric coating agents. A syrup may contain, in addition to the active compounds, sucrose as a sweetening agent and preservatives, dyes, colorings, and flavors. Materials used in preparing these compositions should be pharmaceutically pure and nontoxic in the amounts used.

For purposes of parenteral therapeutic administration, the xanthines can be incorporated into a solution or suspension. These preparations should contain at least 0.1% of the aforesaid compound, but may be varied between 0.5% and about 50% of the weight thereof. The amount of active compound in such compositions is such that a suitable dosage will be obtained. Preferred compositions and preparations according to the present invention are prepared so that a parenteral dosage unit contains between 0.5 mg to 100 mgs of the active compound.

Solutions or suspensions of the xanthines can also include the following components: a sterile diluent, such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic.

While dosage values will vary with the specific disease condition to be alleviated, good results are achieved when the xanthines of formula (I) or formula (II) are administered to a subject requiring such treatment as an effective oral, parenteral or intravenous dose or from 0.1 to 25 mg/kg of body weight per day. A particularly preferred effective amount is about 1.0 mg/kg of body weight per day. In general, daily dosages will vary from 10-1,000 mg, preferably 100-600 mg per day.

It is to be understood, however, that for any particular subject, specific dosage regimens should be adjusted to the individual need and the professional judgment of the person administering or supervising the administration of the xanthines. It is to be further understood that the dosages set forth herein are exemplary only and that they do not, to any extent, limit the scope or practice of the invention.

This invention will now be described in greater detail in the following Examples.

EXAMPLES

To demonstrate the effectiveness of the claimed invention, a compound of the general formula (I) was tested to demonstrate inhibition of the activity of both in vitro-generated human IL-1 and other leukocyte derived cytokines, and purified human IL-1. Though a variety of compounds within the general formula (I) are effective in inhibiting the activities of IL-1 and other leukocyte derived cytokines, they will be exemplified with regard to 1,3-dibutyl 7-(2-oxopropyl)xanthine (DBPOX) as a particularly preferred form of the invention.

Materials

The compound 1,3-dibutyl 7-(2-oxopropyl)xanthine (DBOPX) was prepared according to the procedures described in U.S. Pat. No. 4,242,345. Interleukin-1: Purified human monocyte IL-1(IL-1$\beta$), and diluent were purchased from Cistron Biotechnology, Pine Brook, N.J. The human IL-1 used in these experiments was purified human monocyte interleukin-1. The diluent was PBS-0.1% bovine serum albumin (diluent). IL-1 contained <50 pg/$\mu$g LPS by limulus amebocyte lysate assay. One LAF unit of IL-1 activity is defined as the amount of IL-1 which causes half-maximal incorporation of $^3$H-thymidire by murine [C$^3$H] thymocytes in the presence of concanavalin A [0.5 $\mu$g/ml].

Recombinant human tumor necrosis factor (alpha; rh-TNF): The rh-TNF was purchased from Genzyme Corp, (Boston, Mass.). It was produced in E. coli and was purified by phenyl sepharose chromatography and FPLC to a final purity of greater than 99% as determined by analysis on SDS acrylamide gels stained with both Coomassie Brilliant Blue R250 and silver staining. It has a molecular weight of 36,000 daltons by gel filtration on Superose 12 (FPLC) and consists of 2 dimers of 17,000 daltons each. It was supplied sterile in phosphate-buffered saline containing 0.1% bovine serum albumin as a carrier protein (data supplied by Genzyme). Just before use, the rh-TNF was diluted in Hanks balanced salt solution containing 0.1% human serum albumin.

The other materials were purchased as follows: Dimethyl sulfoxide (DMSO), n-formyl methionyl leucyl phenylalanine (FMLP; 10 mM stock solution in DMSO was stored in 20 $\mu$l aliquots at $-70^\circ$ C.), heparin, cytochrome c type VI from horse heart, and superoxide dismutase from bovine liver (SOD; stock solutions at 5 mg/ml in Hawks balanced salt solution were stored in 100 $\mu$l aliquots at 70$^\circ$ C.) (Sigma Chemical, St. Louis, Mo.); Neutrophil isolation medium (NIM: Los Alamos Diagnostics, Inc., Los Alamos, N.M.); Hanks balanced salt solution (HBSS), Minimum essential medium (MEM) and Medium 199 (M199) (Whittaker, M. A. Bioproducts, Walkersville, Md.); Dulbecco's phosphate buffered saline (PBS; GIBCO Laboratories, Grand Island, N.Y.); Limulus Amebocyte Lysate Test (LAL; Associates of Cape Cod, Inc., Woods Hole, Mass.); scrubbed nylon fiber (3 denier type 200) (Fenwal Laboratories, Deerfield, Ill.); Litex and Agarose type HSA (Accurate Chemical and Scientific Corp., Hicksville, N.Y.).

PMN preparation: Purified PMN (~98% PMN and >95% viable by trypan blue exclusion) containing <1 platelet per 5 PMN and <50 pg/ml LPS (LAL assay) were obtained from normal heparinized (10 Units/ml) venous blood by a one-step ficoll-hypaque separation procedure (NIM). The PMN were washed 3 times with HBSS or MEM. Residual RBC were lysed by hypotonic lysis for the PMN oxidative burst assays.

Mononuclear leukocyte conditioned medium: Purified human IL-1 was obtained from Cistron Technology, Pinebrook, N.J. As is known, the production of IL-1 from macrophages or circulating monocytes can be stimulated by the presence of bacterial lipolysaccharides. Stites et al., Basic and Clinical Immunology, page 87 (1984). Accordingly, in vitro-generated IL-1 was obtained through the incubation of mononuclear leukocytes. Mononuclear leukocytes ($3 \times 10^6$/ml) from ficoll-hypaque separation were incubated in a medium 199 (M199) containing 10% fresh autologous serum with or without lipolysaccharides 5 ng/ml or with or without supernatant from C. albicans culture for 18 hours at 37$^\circ$ C. (10% CO$_2$) in LAB-TEK Flaskettes (Miles Inc. Naperville, Ill. The suspension was centrifuged (150 g $\times$ 10 minutes) and the supernatant filtered (0.45 micron 4) and frozen ($-70^\circ$ C.).

Mononuclear leukocyte conditioned media was prepared by incubating washed mixed mononuclear leukocytes ($3 \times 10^6$/ml) from NIM separation in medium 199 (M199) containing 10% fresh autologous serum for 18 hrs. at 37$^\circ$ C. (10% CO$_2$) with or without LPS (5 ng/ml) in Lab-Tek Flaskettes (Miles Inc., Naperville, Ill.) The suspension was centrifuged 150 g $\times$ 10 min., and then the supernatant was filtered (0.45 micron pore) and frozen ($-70^\circ$ C.).

Statistics: The results are reported as the mean±SEM. P-values were determined by using a 2-tailed student t-test.

EXAMPLE 1

Cell Chemotaxis

A. Effect of DBOPX

Chemotaxis under agarose was quantitated by the method of Nelson et al., J. Immunol., 115, 1650–1656 (1975). Purified PMN ($5 \times 10^6$ PMN) were incubated for 15 min. at 37° C. in a total volume of (40 μl, 60 μl, 90 μl) HBSS with or without DBOPX (as specified) and then were incubated for 30 min. more at 37° C. in a total volume of 0.1 ml with or without LPS (0.2 ng/40 μl), LPS stimulated mononuclear leukocyte conditioned medium (40 μl), IL-1 (16 units/60 μl) d luent (60 μl) or rh-TNF (100 units/10 μl). The migration to FMLP (100 nM) was measured after 2 hrs. incubation at 37° C.

DBOPX increased chemotaxis inhibited by IL-1, TNF, or LPS stimulated mononuclear leukocyte conditioned medium as shown in FIGS. 1, 2 and 3.

B. Effect of Pentoxifylline

As reported below, not only is the adherence of polymorphonuclear neutrophil (PMN) caused by IL-1 inhibited by the compounds of general formula (II), but the inhibition of normal chemotaxis of PMN caused by IL-1 was also reduced by the presence of the compounds of the general formula (II). PMN chemotaxis was assayed under agarose by the method of Nelson, Quie and Simmons. Neutrophils were placed in the center well of a triplet and the chemoattractant (FMLP $10^{-7}$M) was placed in one outer well and M199 was placed in the opposite well. Following 2 hour incubation at 37° C. the plates were fixed and stained and the zones of migration measured. The direced migration was the distance in mm that the leading front of PMN moved toward the chemoattractant.

1. Effect of LPS stimulated mononuclear leukocyte conditioned medium on PMN directed migration: Modulation of this effect by pentoxifylline Pure PMN ($5 \times 10^6$/ml) were incubated for 30 minutes at 37° C. with or without pentoxifylline (0.1 or 50 micrograms/ml) in M199 2% serum, "NO ADD", M199 2% serum containing LPS (1 ng/ml), "LPS", mononuclear leukocyte conditioned M199 2% serum, "CONT KINE", or LPS stimulated mononuclear leukocyte conditioned M199 2% serum, "LPS KINE". The PMN were concentrated 10 fold prior to application in the under agarose chemotaxis assay.

Figure 8:
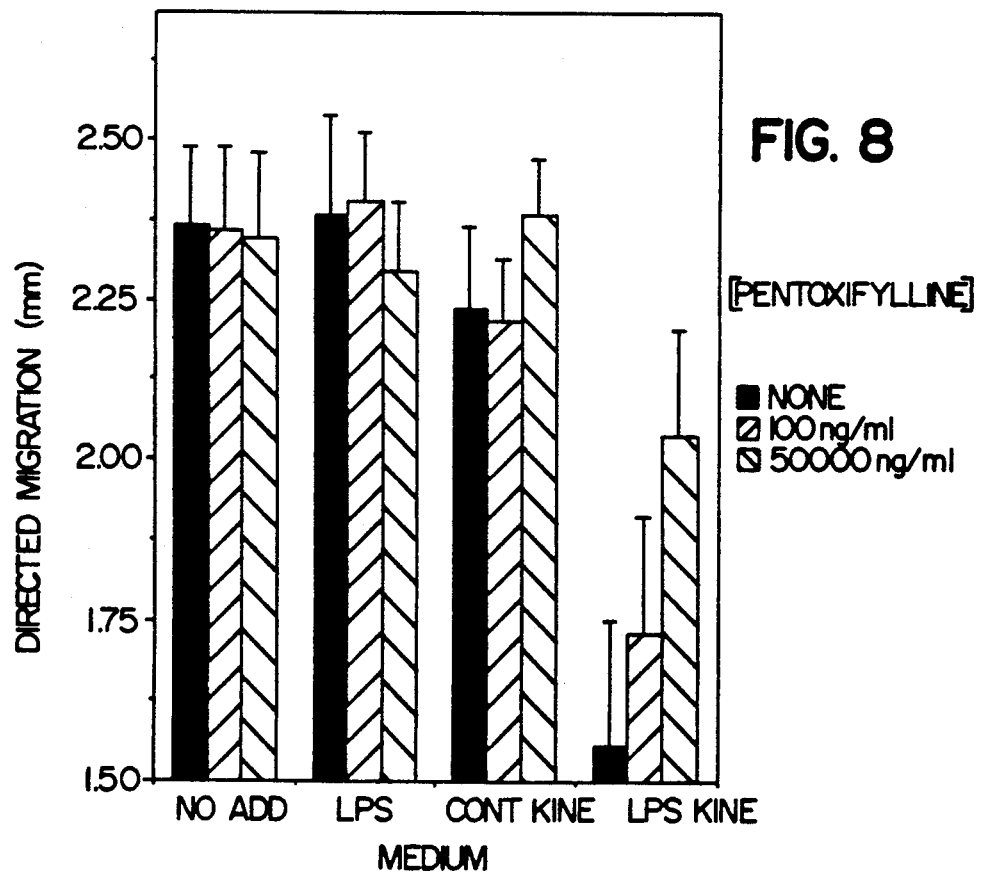
FIG. 8 shows modulation by pentoxifylline of the effect of LPS stimulated mononuclear leukocyte conditioned medium on PMN directed migration.

Pentoxifylline (50 and 0.1 micrograms/ml) increased directed migration inhibited by "LPS KINE". (See, FIG. 8.)

2. Effect of C. albicans stimulated mononuclear leukocyte conditioned medium on PMN directed migration: Modulation of this effect by pentoxifylline Pure PMN ($5 \times 10^6$/ml) were incubated for 30 minutes at 37° C. with or without pentoxifylline (0.1 or 50 micrograms/ml) in M199 5% serum, "NO ADD", M199 5% serum containing supernatant from C. albicans culture, "C.ALB", mononuclear leukocyte conditioned M199 5% serum, "CONT KINE", or C. albicans stimulated mononuclear leukocyte conditioned M199 5% serum, "C. ALB KINE". The PMN were concentrated 10 fold prior to application in the under agarose chemotaxis assay.

Figure 9:
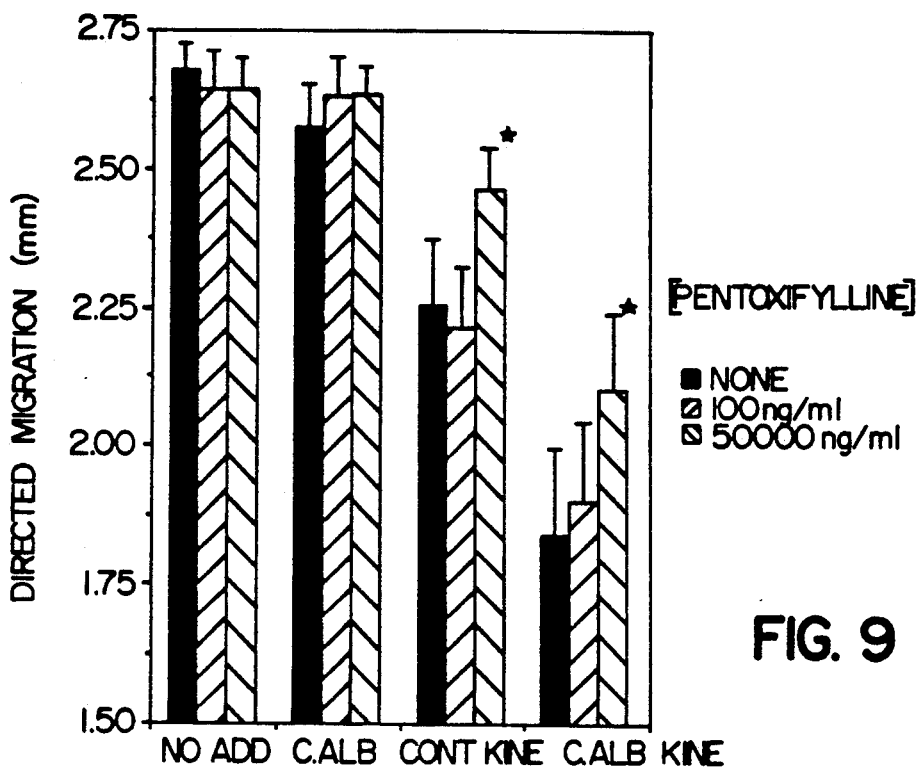
FIG. 9 shows modulation by pentoxifylline of the effect of *C. albicans* stimulated mononuclear leukocyte conditioned medium on PMN directed migration.

Pentoxifylline (50 micrograms/ml) increased directed migration inhibited by "C. ALB KINE" and "CONT KINE". (See, FIG. 9.)

3. Effect of interleukin-1 on PMN directed migration: Modulation of this effect by pentoxifylline Pure PMN ($5 \times 10^6$/ml) were incubated for 30 minutes at 37° C. with or without pentoxifylline (0.1 or 50 micrograms/ml) in minimum essential medium (MEM) or MEM containing IL-1 at 0 to 80 Units/ml. The PMN were concentrated 10 fold prior to application in the under agarose chemotaxis assay.

Figure 10:
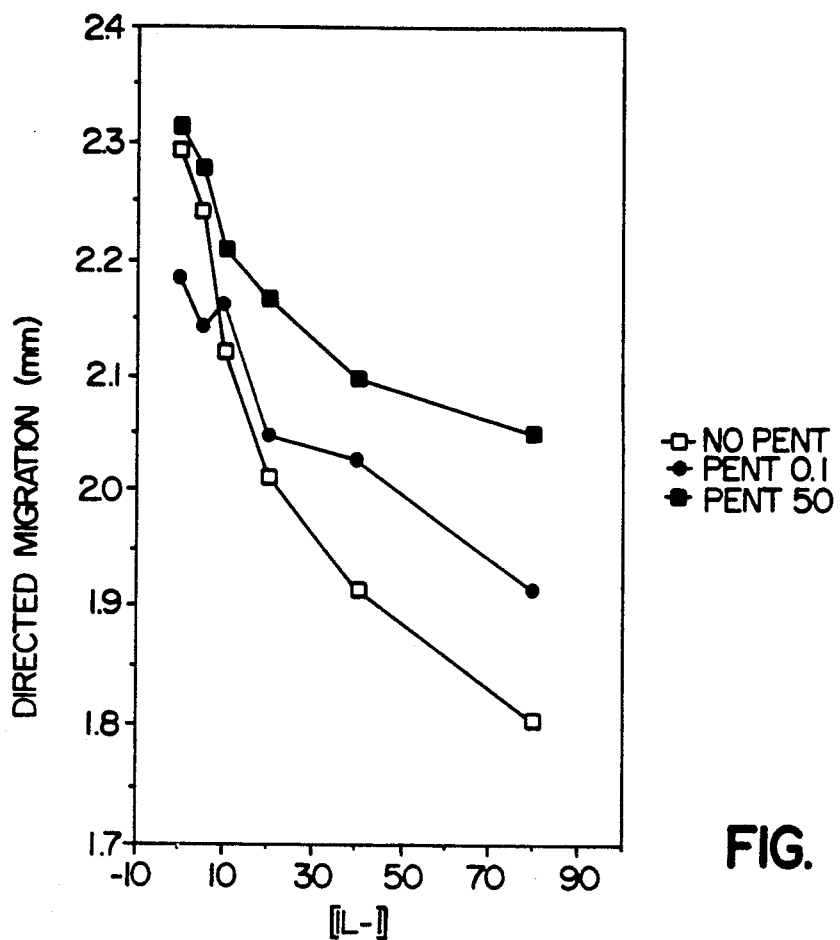
FIG. 10 shows modulation by pentoxifylline of the effect of IL-1 on PMN directed migration.

Pentoxifylline (0.1 or 50 micrograms/ml) increased directed migration inhibited by interleukin-1. (See, FIG. 10.)

EXAMPLE 2

PMN Adherence To Nylon

A. Effect of DBOPX

PMN adherence was determined by a modified method of MacGregor. Purified PMN were incubated in 0.1 ml medium 199 with or without DBOPX (as specified) containing LPS, or LPS stimulated mononuclear leukocyte conditioned medium for 30 min. at 37° C. After incubation HBSS (0.9 ml) and autologous serum (10 μl/ml were added to the cell suspensions. The cell suspensions were applied to the top of pre-warmed (37° C.) 60 mg nylon columns packed to the 0.3 ml mark on a plastic 1 ml syringe. The columns were allowed to elute for 30 min. at 37° C. and the number of PMN in both the pre- and post-column samples counted. The results are expressed as percent PMN adherence to the nylon.

DBOPX (10 ug/ml) diminished PMN adherence to nylon augmented by LPS stimulated mononuclear leukocyte conditioned medium as shown in FIG. 4.

B. Effect of Pentoxifylline

1. The effect of LPS stimulated mononuclear leukocyte conditioned medium on PMN adherence: How pentoxifylline modulates this effect Purified PMN ($5 \times 10^6$/ml) were incubated 30 minutes at 37° C. in M199, "NONE", LPS (1 ng/ml), "LPS", mononuclear leukocyte conditioned medium, "CONT KINES", or in "LPS KINES". One ml was pipetted onto the top of a nylon fiber column and incubated at 37° C. for 30 minutes. The PMN in the effluent samples were counted and the percent adherence of PMN on the column determined.

Figure 11:
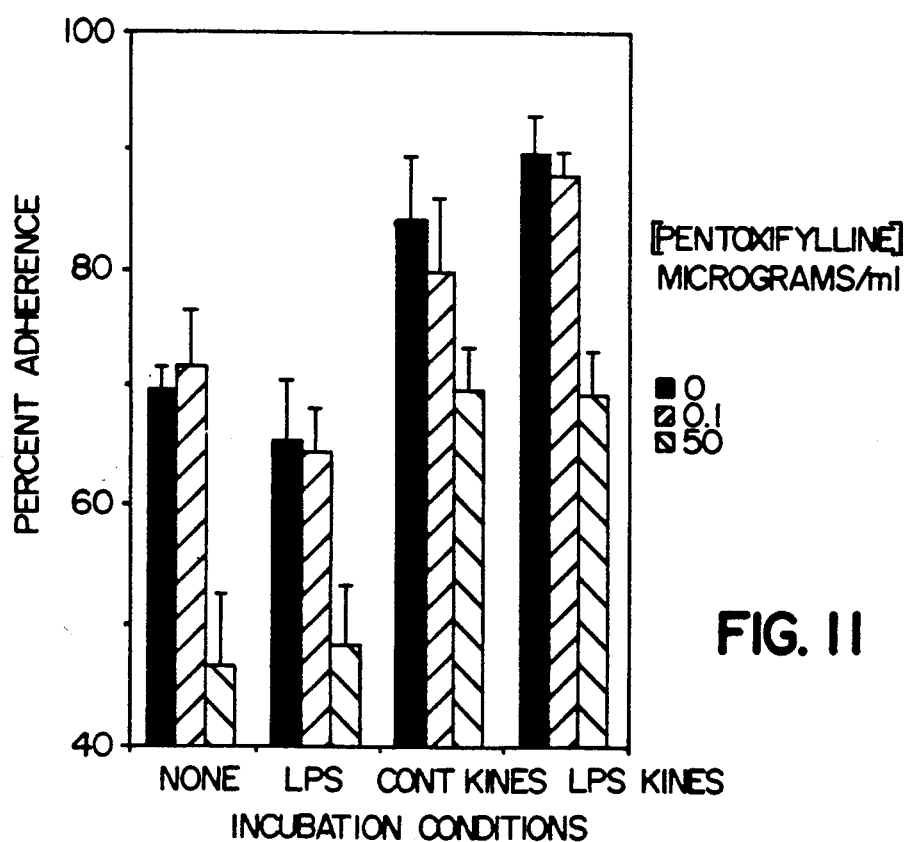
FIG. 11 shows modulation by pentoxifylline of the effect of LPS stimulated mononuclear leukocyte conditioned medium on PMN adherence.

Pentoxifylline (50 micrograms/ml) decreased PMN adherence under all four experimental conditions. (See, FIG. 11.)

2. The effect of IL-1 and LPS stimulated mononuclear leukocyte conditioned medium on PMN adherence: How pentoxifylline modulates this effect Two tenths ml of purified PMN ($1 \times 10^7$/ml) was incubated 30 minutes at 37° C. in M199, "control", or M199 containing IL-1 (800 U/ml), "IL-1", or in LPS stimulated mononuclear leukocyte conditioned medium, "LPS KINE", with or without pentoxifylline (0.1 or 50 micrograms/ml).

Following incubation the samples were diluted to a final concentration of $5 \times 10^6$/ml with M199 (2% serum). One ml was placed onto the top of a nylon fiber column and incubated at 37° C. for 30 minutes. The PMN in the effluent samples were counted and percent adherence of PMN on the nylon column calculated.

Figure 12:
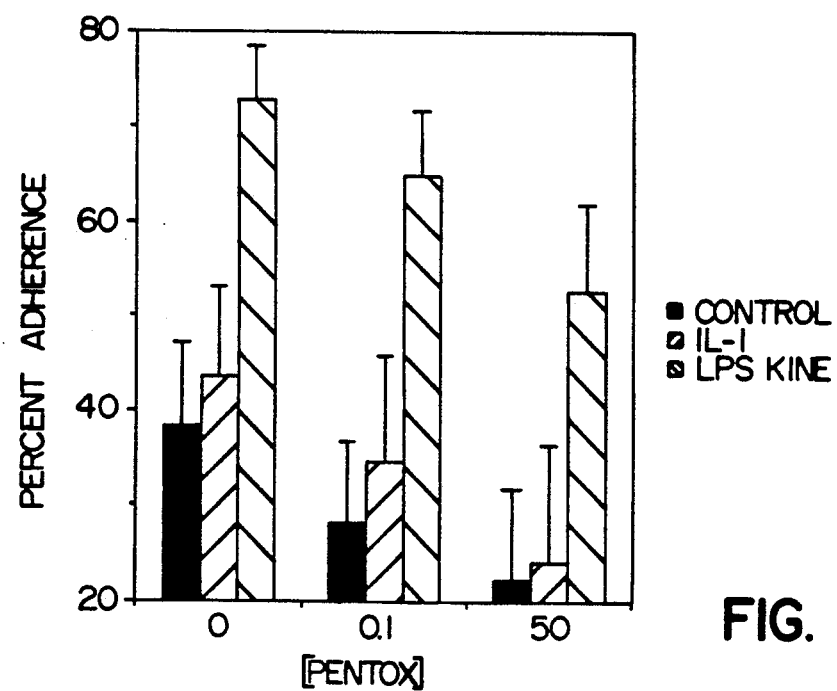
FIG. 12 shows modulation by pentoxifylline of the effect of IL-1 and LPS stimulated mononuclear leukocyte conditioned medium on PMN adherence.

Both pentoxifylline 0.1 and 50 micrograms/ml decreased PMN nylon adherence under the three experimental conditions. (See, FIG. 12.)

EXAMPLE 3

PMN Oxidative Burst Effect of DBOPX

Cytochrome c reduction: Purified PMN (2 to $4 \times 10^6$) were suspended in a total volume of 80 μl HBSS with or without DBPOX (as specified) and were incubated for 15 min. at 37° C. with or without SOD (200 units/sample). IL-1 (5 Units/20 μl), LPS (0.1 ng/20 μl), LPS stimulated mononuclear leukocyte conditioned medium (20 μl), or IL-1 diluent were then added and the cells incubated for 30 min. more at 37° C.

HBSS (0.4 ml) and cytochrome c (50 μ; final concentration 120 μM) were added to all samples. FMLP (100 nM) was added. The samples were incubated for 10 min. more at 37° C. then iced, and centrifuged ($2000 \times g$ for 10 min.). The optical density of the supernatants was read at a wavelength of 550 nm and the nmoles of SOD-inhibitable superoxide/$10^6$ PMN calculated using the extinction coefficient of $2.11 \times 10^4$ cm2/mmole (reduced-oxidized).

DBOPX (0.1–100 ug/ml) decreased PMN superoxide production when the PMN had been primed with IL-1, TNF, and stimulated with FMLP as is evident from FIG. 5. DBOPX decreased PMN superoxide production when the PMN had been primed with LPS stimulated mononuclear leukocyte conditioned medium as shown in FIG. 6.

EXAMPLE 4

PMN Degranulation (Release of Lysozyme) Effect of DBOPX

PMN ($4 \times 10^6$) were suspended in HBSS (0.08 ml) with or without DBOPX (as specified) and incubated for 15 min. (37° C.). Then LPS (0.01 ng/0.02 ml) or LPS stimulated mononuclear leukoycte conditioned medium (0.02 ml) was added to the samples and incubated 30 min. more. HBSS (0.9 ml) and FMLP (10 μl; $10^{-7}$ M final concentration) was added to all samples. The samples were incubated for 10 min. and then iced and centrifuged ($2000 \times g$ for 10 min.). The supernatants were poured off and the lysozyme content determined by measurement of changes in the optical density of a suspension of *Micrococcus lysodeikticus* after addition of the supernatants using the method described in *J. Bacteriol.*, 58:731-736 (1949). DBOPX decreased the release of lysozyme from PMN primed with LPS stimulated mononuclear leukocyte conditioned medium and then stimulated with FMLP as is evident from FIG. 7.

Numerous modifications and variations of the present invention are possible in light of the above teachings. It is, therefore, to be understood that within the scope of the appended claims, the invention can be practiced otherwise than as specifically described herein.

What is claimed is:

1. A method of inhibiting immune response in a mammal, wherein the method comprises administering to the mammal an amount of at least one 7-(oxoalkyl) 1,3-dialkyl xanthine of the formula:

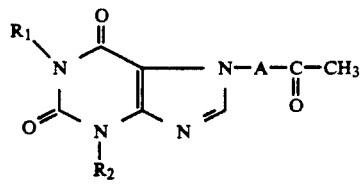

in which
R1 and R2 are the same or different and are independently selected from the group consisting of straight-chain or branched alkyl radicals with 2 to 6 carbon atoms, cyclohexyl, straight-chain or branched chain alkoxyalkyl and hydroxyalkyl radicals;

A represents a hydrocarbon radical with up to 4 carbon atoms, which can be substituted by a methyl group; and wherein said amount is effective in inhibiting immune response by inhibiting the activity of IL-1, TNF, or other leukocyte derived cytokines on polymorphonuclear leukocytes.

2. A method of inhibiting immune response in a mammal, wherein the method comprises administering to the mammal an amount of at least one 7-(oxoalkyl) 1,3-dialkyl xanthine of the formula:

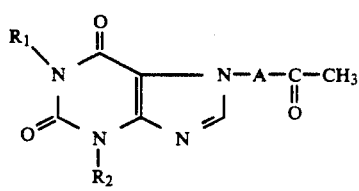

in which
R1 and R2 are the same or different and are independently selected from the group consisting of straight-chain or branched alkyl radicals with 2 to 6 carbon atoms, cyclohexyl, straight-chain or branched chain alkoxyalkyl and hydroxyalkyl radicals;

A represents a hydrocarbon radical with up to 4 carbon atoms, which can be substituted by a methyl group; and wherein said amount is effective in inhibiting immune response by inhibiting the activity of IL-1, TNF, or other leukocyte derived cytokines on neutrophils.

3. A method of inhibiting immune response in a mammal, wherein the method comprises administering to the mammal an amount of at least one 7-(oxoalkyl) 1,3-dialkyl xanthine of the formula:

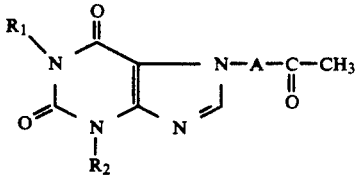

in which
R1 and R2 are the same or different and are independently selected from the group consisting of straight-chain or branched alkyl radicals with 2 to 6 carbon atoms, cyclohexyl, straight-chain or branched chain alkoxyalkyl and hydroxyalkyl radicals;

A represents a hydrocarbon radical with up to 4 carbon atoms, which can be substituted by a methyl group; and wherein said amount is effective in inhibiting immune response by inhibiting the activity of IL-1, TNF, or other leukocyte derived cytokines on mononuclear phagocytes.

4. A method of inhibiting immune response in a mammal, wherein the method comprises administering to the mammal an amount of at least one 7-(oxoalkyl) 1,3-dialkyl xanthine of the formula:

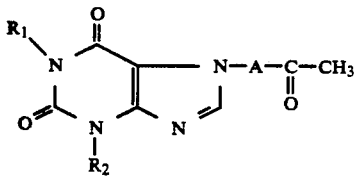

in which

R$_1$ and R$_2$ are the same or different and are independently selected from the group consisting of straight-chain or branched alkyl radicals with 2 to 6 carbon atoms, cyclohexyl, straight-chain or branched chain alkoxyalkyl and hydroxyalkyl radicals;

A represents a hydrocarbon radical with up to 4 carbon atoms, which can be substituted by a methyl group; and wherein said amount is effective in inhibiting immune response by inhibiting the activity of IL-1, TNF, or other leukocyte derived cytokines on monocytes.

5. A method of inhibiting immune response in a mammal, wherein the method comprises administering to the mammal an amount of at least one 7-(oxoalkyl) 1,3-dialkyl xanthine of the formula:

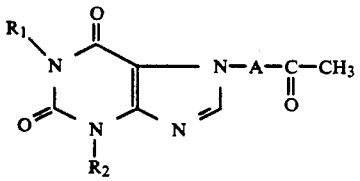

in which

R$_1$ and R$_2$ are the same or different and are independently selected from the group consisting of straight-chain or branched alkyl radicals with 2 to 6 carbon atoms, cyclohexyl, straight-chain or branched chain alkoxyalkyl and hydroxyalkyl radicals;

A represents a hydrocarbon radical with up to 4 carbon atoms, which can be substituted by a methyl group; and wherein said amount is effective in inhibiting immune response by inhibiting the activity of IL-1, TNF, or other leukocyte derived cytokines on macrophages.

6. A method of inhibiting immune response in a mammal, wherein the method comprises administering to the mammal an amount of at least one 7-(oxoalkyl) 1,3-dialkyl xanthine of the formula:

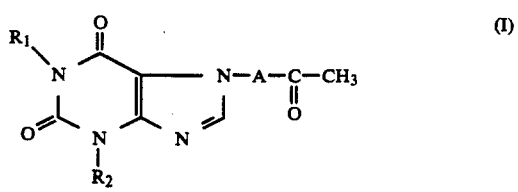

in which

R$_1$ and R$_2$ are the same or different and are independently selected from the group consisting of straight-chain or branched alkyl radicals with 2 to 6 carbon atoms, cyclohexyl, straight-chain or branched chain alkoxyalkyl and hydroxyalkyl radicals;

A represents a hydrocarbon radical with up to 4 carbon atoms, which can be substituted by a methyl group; and wherein said amount is effective in inhibiting immune response by inhibiting the activity of IL-1, TNF, or other leukocyte derived cytokines on lymphocytes.

7. A method of alleviating an adverse condition in a mammal mediated by IL-1, TNF, or other leukocyte derived cytokines, which comprises administering to the mammal an amount of at least one 7-(oxoalkyl) 1,3-dialkyl xanthine of the formula:

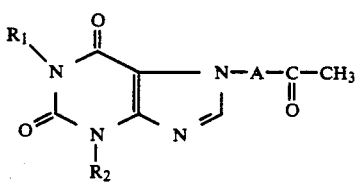

in which

R$_1$ and R$_2$ are the same or different and are independently selected from the group consisting of straight-chain or branched alkyl radicals with 2 to 6 carbon atoms, cyclohexyl, straight-chain or branched chain alkoxyalkyl and hydroxyalkyl radicals;

A represents a hydrocarbon radical with up to 4 carbon atoms, which can be substituted by a methyl group; and wherein said amount is effective in alleviating the activity, which mediates the adverse condition, of IL1, TNF, or other leukocyte derived cytokines.

8. A method of inhibiting immune response in a mammal, wherein the method comprises administering to the mammal an amount of at least one xanthine of the formula:

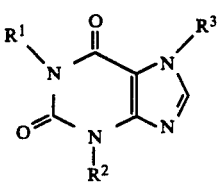

wherein at least one of R$^1$ and R$^3$ is either
a) a branched hydroxyalkyl group of the formula $$(CH_2)_n - \underset{\underset{OH}{|}}{\overset{\overset{R^4}{|}}{C}} - CH_3,$$

in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or b) an oxoallyl group of the formula $$R^6 - \overset{\overset{O}{\|}}{C} - (CH_2)_p$$

wherein $R^6$ is $C_1$-$C_6$ and p is 2, 3 or 4, the remaining $R^1$ or $R^3$ being as defined above, and $R^2$ is a $C_1$-$C_4$ alkyl group;

wherein said amount is effective in inhibiting immune response by inhibiting the activity of IL-1, TNF, or other leukocyte derived cytokines on polymorphonuclear leukocytes.

9. A method of inhibiting immune response in a mammal, wherein the method comprises administering to the mammal an amount of at least one xanthine of the formula:

(II)

wherein at least one of $R^1$ and $R^3$ is either
a) a branched hydroxyalkyl group of the formula $$(CH_2)_n - \underset{\underset{OH}{|}}{\overset{\overset{R^4}{|}}{C}} - CH_3,$$

in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or b) an oxoallyl group of the formula $$R^6 - \overset{\overset{O}{\|}}{C} - (CH_2)_p$$

wherein $R^6$ is $C_1$-$C_6$ and p is 2, 3 or 4, the remaining $R^1$ or $R^3$ being as defined above, and $R^2$ is a $C_1$-$C_4$ alkyl group;

wherein said amount is effective in inhibiting immune response by inhibiting the activity of IL-1, TNF, or other leukocyte derived cytokines on neutrophils.

10. A method of inhibiting immune response in a mammal, wherein the method comprises administering to the mammal an amount of at least one xanthine of the formula:

(II)

wherein at least one of $R^1$ and $R^3$ is either
a) a branched hydroxyalkyl group of the formula $$(CH_2)_n - \underset{\underset{OH}{|}}{\overset{\overset{R^4}{|}}{C}} - CH_3,$$

in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or b) an oxoallyl group of the formula $$R^6 - \overset{\overset{O}{\|}}{C} - (CH_2)_p$$

wherein $R^6$ is $C_1$-$C_6$ and p is 2, 3 or 4, the remaining $R^1$ or $R^3$ being as defined above, and $R^2$ is a $C_1$-$C_4$ alkyl group;

wherein said amount is effective in inhibiting immune response by inhibiting the activity of IL-1, TNF, or other leukocyte derived cytokines on mononuclear phagocytes.

11. A method of inhibiting immune response in a mammal, wherein the method comprises administering to the mammal an amount of at least one 7-(oxoalkyl) 1,3-dialkyl xanthine of the formula:

(II)

wherein at least one of $R^1$ and $R^3$ is either
a) a branched hydroxyalkyl group of the formula $$(CH_2)_n - \underset{\underset{OH}{|}}{\overset{\overset{R^4}{|}}{C}} - CH_3,$$

in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or b) an oxoallyl group of the formula

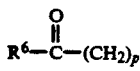

wherein $R^6$ is $C_1$-$C_6$ and p is 2, 3 or 4, the remaining $R^1$ or $R^3$ being as defined above, and $R^2$ is a $C_1$-$C_4$ alkyl group;

wherein said amount is effective in inhibiting immune response by inhibiting the activity of IL-1, TNF, or other leukocyte derived cytokines on monocytes.

12. A method of inhibiting immune response in a mammal, wherein the method comprises administering to the mammal an amount of at least one xanthine of the formula:

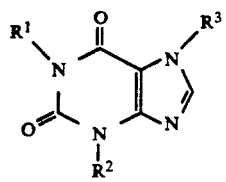 (II)

wherein at least one of $R^1$ and $R^3$ is either
a) a branched hydroxyalkyl group of the formula

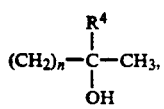

in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or b) an oxoallyl group of the formula

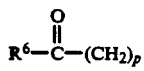

wherein $R^6$ is $C_1$-$C_6$ and p is 2, 3 or 4, the remaining $R^1$ or $R^3$ being as defined above, and $R^2$ is a $C_1$-$C_4$ alkyl group;

wherein said amount is effective in inhibiting immune response by inhibiting the activity of IL-1, TNF, or other leukocyte derived cytokines on macrophages.

13. A method of inhibiting immune response in a mammal, wherein the method comprises administering to the mammal an amount of at least one xanthine of the formula:

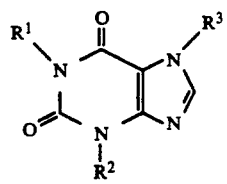 (II)

wherein at least one of $R^1$ and $R^3$ is either
a) a branched hydroxyalkyl group of the formula

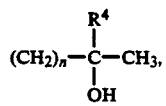

in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or b) an oxoallyl group of the formula

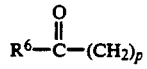

wherein $R^6$ is $C_1$-$C_6$ and p is 2, 3 or 4, the remaining $R^1$ or $R^3$ being as defined above, and $R^2$ is a $C_1$-$C_4$ alkyl group;

wherein said amount is effective in inhibiting immune response by inhibiting the activity of IL-1, TNF, or other leukocyte derived cytokines on lymphocytes.

14. A method of alleviating an adverse condition in a mammal mediated by IL-1, TNF, or other leukocyte derived cytokines, which comprises administering to the mammal an amount of at least one xanthine of the formula:

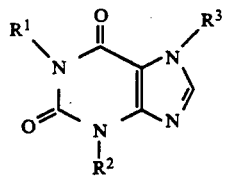 (II)

wherein at least one of $R^1$ and $R^3$ is either
a) a branched hydroxyalkyl group of the formula

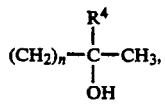

in which $R^4$ stands for an alkyl group with 1 to 3 carbon atoms and n stands for a whole number from 2 to 5, the other $R^1$ or $R^3$ group that may optionally be present stands for a hydrogen atom or an aliphatic hydrocarbon group $R^5$ with up to 6 carbon atoms, whose carbon chain may be interrupted by up to 2 oxygen atoms or may be substituted with a hydroxy or oxo group, or b) an oxoallyl group of the formula

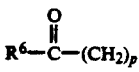

wherein $R^6$ is $C_1$–$C_6$ and p is 2, 3 or 4, the remaining $R^1$ or $R^3$ being as defined above, and $R^2$ is a $C_1$–$C_4$ alkyl group;

wherein said amount is effective in alleviating the activity, which mediates the adverse condition, of IL-1, TNF, or other leukocyte derived cytokines.

15. A method of alleviating an adverse condition in a mammal mediated by IL-1, TNF, or other leukocyte derived cytokines, which comprises administering to the mammal an amount of at least one xanthine of the formula:

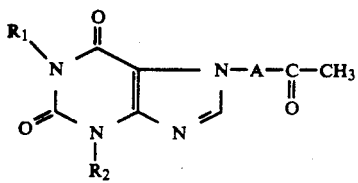
(I)

in which $R_1$ and $R_2$ are the same or different and are independently selected from the group consisting of straight-chain or branched alkyl radicals with 2 to 6 carbon atoms, cyclohexyl, straight-chain or branched chain alkoxyalkyl and hydroxyalkyl radicals;

A represents a hydrocarbon radical with up to 4 carbon atoms, which can be substituted by a methyl group; and wherein said amount is effective in alleviating the activity, which mediates the adverse condition, of IL-1, TNF, or other leukocyte derived cytokines.

16. A method of inhibiting immune response in a mammal, wherein the method comprises administering to the mammal an amount of at least one xanthine of the formula:

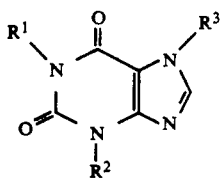
(II)

wherein $R_1$ and $R_2$ and $R_3$ are the same or different and are selected from the group consisting of
 (a) $C_1$–$C_6$ straight or branched chain alkyl;
 (b) $C_1$–$C_6$ straight or branched chain alkoxyalkyl;
 (c) $C_1$–$C_6$ straight or $C_1$–$C_9$ branched chain hydroxyalkyl;
 (d) $C_1$–$C_6$ aliphatic hydrocarbon group whose carbon chain may be interrupted by up to 2 oxygen atoms;
 (e) $C_3$–$C_{11}$ oxoalkyl group;
 and in addition $R_1$ and $R_2$ can be cyclohexyl;
wherein said amount is effective in inhibiting immune response by inhibiting the activity of IL-1, TNF, or other leukocyte derived cytokines on polymorphonuclear leukocytes.

17. A method of inhibiting immune response in a mammal, wherein the method comprises administering to the mammal an amount of at least one xanthine of the formula:

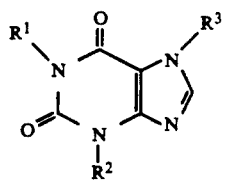
(II)

wherein $R_1$ and $R_2$ and $R_3$ are the same or different and are selected from the group consisting of
 (a) $C_1$–$C_6$ straight or branched chain alkyl;
 (b) $C_1$–$C_6$ straight or branched chain alkoxyalkyl;
 (c) $C_1$–$C_6$ straight or $C_1$–$C_9$ branched chain hydroxyalkyl;
 (d) $C_1$–$C_6$ aliphatic hydrocarbon group whose carbon chain may be interrupted by up to 2 oxygen atoms;
 (e) $C_3$–$C_{11}$ oxoalkyl group;
 and in addition $R_1$ and $R_2$ can be cyclohexyl;
wherein said amount is effective in inhibiting immune response by inhibiting the activity of IL-1, TNF, or other leukocyte derived cytokines on neutrophils.

18. A method of inhibiting immune response in a mammal, wherein the method comprises administering to the mammal an amount of at least one xanthine of the formula:

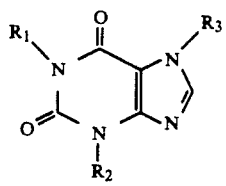

wherein $R_1$ and $R_2$ and $R_3$ are the same or different and are selected from the group consisting of
 (a) $C_1$–$C_6$ straight or branched chain alkyl;
 (b) $C_1$–$C_6$ straight or branched chain alkoxyalkyl;
 (c) $C_1$–$C_6$ straight or $C_1$–$C_9$ branched chain hydroxyalkyl; and in addition $R_1$ and $R_2$ can be cyclohexyl;
 (d) $C_1$–$C_6$ aliphatic hydrocarbon group whose carbon chain may be interrupted by up to 2 oxygen atoms;
 (e) $C_3$–$C_{11}$ oxoalkyl group;
wherein said amount is effective in inhibiting immune response by inhibiting the activity of IL-1, TNF, or other leukocyte derived cytokines on mononuclear phagocytes.

19. A method of inhibiting immune response in a mammal, wherein the method comprises administering to the mammal an amount of at least one 7-(oxoalkyl) 1,3-dialkyl xanthine of the formula:

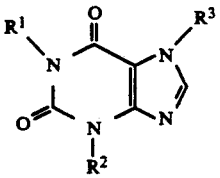

wherein
R$_1$ and R$_2$ and R$_3$ are the same or different and are selected from the group consisting of
(a) C$_1$-C$_6$ straight or branched chain alkyl;
(b) C$_1$-C$_6$ straight or branched chain alkoxyalkyl;
(c) C$_1$-C$_6$ straight or C$_1$-C$_9$ branched chain hydroxyalkyl;
(d) C$_1$-C$_6$ aliphatic hydrocarbon group whose carbon chain may be interrupted by up to 2 oxygen atoms;
(e) C$_3$-C$_{11}$ oxoalkyl group;
and in addition R$_1$ and R$_2$ can be cyclohexyl;
wherein said amount is effective in inhibiting immune response by inhibiting the activity of IL-1, TNF, or other leukocyte derived cytokines on monocytes.

20. A method of inhibiting immune response in a mammal, wherein the method comprises administering to the mammal an amount of at least one xanthine of the formula:

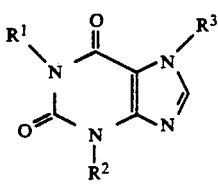

wherein
R$_1$ and R$_2$ and R$_3$ are the same or different and are selected from the group consisting of
(a) C$_1$-C$_6$ straight or branched chain alkyl;
(b) C$_1$-C$_6$ straight or branched chain alkoxyalkyl;
(c) C$_1$-C$_6$ straight or C$_1$-C$_9$ branched chain hydroxyalkyl;
(d) C$_1$-C$_6$ aliphatic hydrocarbon group whose carbon chain may be interrupted by up to 2 oxygen atoms;
(e) C$_3$-C$_{11}$ oxoalkyl group;
and in addition R$_1$ and R$_2$ can be cyclohexyl;
wherein said amount is effective in inhibiting immune response by inhibiting the activity of IL-1, TNF, or other leukocyte derived cytokines on macrophages.

21. A method of inhibiting immune response in a mammal, wherein the method comprises administering to the mammal an amount of at least one xanthine of the formula:

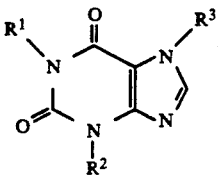

wherein

R$_1$ and R$_2$ and R$_3$ are the same or different and are selected from the group consisting of
(a) C$_1$-C$_6$ straight or branched chain alkyl;
(b) C$_1$-C$_6$ straight or branched chain alkoxyalkyl;
(c) C$_1$-C$_6$ straight or C$_1$-C$_9$ branched chain hydroxyalkyl;
(d) C$_1$-C$_6$ aliphatic hydrocarbon group whose carbon chain may be interrupted by up to 2 oxygen atoms;
(e) C$_3$-C$_{11}$ oxoalkyl group;
and in addition R$_1$ and R$_2$ can be cyclohexyl;
wherein said amount is effective in inhibiting immune response by inhibiting the activity of IL-1, TNF, or other leukocyte derived cytokines on lymphocytes.

22. A method of alleviating an adverse condition in a mammal mediated by IL-1, TNF, or other leukocyte derived cytokines, which comprises administering to the mammal an amount of at least one xanthine of the formula:

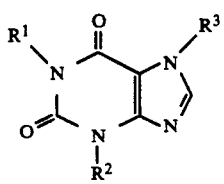

wherein
R$_1$ and R$_2$ and R$_3$ are the same or different and are selected from the group consisting of
(a) C$_1$-C$_6$ straight or branched chain alkyl;
(b) C$_1$-C$_6$ straight or branched chain alkoxyalkyl;
(c) C$_1$-C$_6$ straight or C$_1$-C$_9$ branched chain hydroxyalkyl;
(d) C$_1$-C$_6$ aliphatic hydrocarbon group whose carbon chain may be interrupted by up to 2 oxygen atoms;
(e) C$_3$-C$_{11}$ oxoalkyl group;
and in addition R$_1$ and R$_2$ can be cyclohexyl;
wherein said amount is effective in alleviating the activity, which mediates the adverse condition, of IL-1, TNF, or other leukocyte derived cytokines.

23. The method as claimed in any one of claims 16–22, wherein R$_1$ is a hydroxyalkyl radical.

24. The method as claimed in claim 23, wherein R$_2$ is a straight-chain or branched alkyl radical with 1 to 6 carbon atoms.

25. The method as claimed in claim 24, wherein the R$_3$ group stands for an aliphatic hydrocarbon group R$_5$ with up to 6 carbon atoms.

26. A method of inhibiting immune response in a mammal, wherein the method comprises administering to the mammal an amount of at least one xanthine of the formula:

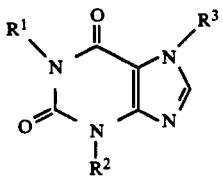

wherein
R$_1$ and R$_2$ and R$_3$ are the same or different and are selected from the group consisting of (a) $C_1$-$C_6$ straight or branched chain alkyl;

(b) $C_1$-$C_6$ straight or branched chain alkoxyalkyl;

(c) $C_1$-$C_6$ straight or $C_1$-$C_9$ branched chain hydroxyalkyl;

and in addition $R_1$ and $R_2$ can be cyclohexyl;

wherein said amount is effective in inhibiting immune response by inhibiting the activity of IL-1, TNF, or other leukocyte derived cytokines on polymorphonuclear leukocytes.

27. A method of inhibiting immune response in a mammal, wherein the method comprises administering to the mammal an amount of at least one xanthine of the formula:

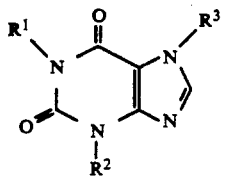

(II)

wherein $R_1$ and $R_2$ and $R_3$ are the same or different and are selected from the group consisting of (a) $C_1$-$C_6$ straight or branched chain alkyl;

(b) $C_1$-$C_6$ straight or branched chain alkoxyalkyl;

(c) $C_1$-$C_6$ straight or $C_1$-$C_9$ branched chain hydroxyalkyl;

and in addition $R_1$ and $R_2$ can be cyclohexyl;

wherein said amount is effective in inhibiting immune response by inhibiting the activity of IL-1, TNF, or other leukocyte derived cytokines on neutrophils.

28. A method of inhibiting immune response in a mammal, wherein the method comprises administering to the mammal an amount of at least one xanthine of the formula:

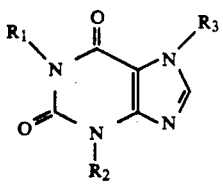

wherein $R_1$ and $R_2$ and $R_3$ are the same or different and are selected from the group consisting of (a) $C_1$-$C_6$ straight or branched chain alkyl;

(b) $C_1$-$C_6$ straight or branched chain alkoxyalkyl;

(c) $C_1$-$C_6$ straight or $C_1$-$C_9$ branched chain hydroxyalkyl;

and in addition $R_1$ and $R_2$ can be cyclohexyl;

wherein said amount is effective in inhibiting immune response by inhibiting the activity of IL-1, TNF, or other leukocyte derived cytokines on mononuclear phagocytes.

29. A method of inhibiting immune response in a mammal, wherein the method comprises administering to the mammal an amount of at least one 7-(oxoalkyl) 1,3-dialkyl xanthine of the formula:

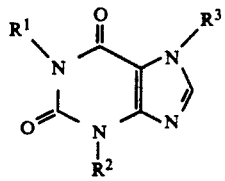

(II)

wherein $R_1$ and $R_2$ and $R_3$ are the same or different and are selected from the group consisting of (a) $C_1$-$C_6$ straight or branched chain alkyl;

(b) $C_1$-$C_6$ straight or branched chain alkoxyalkyl;

(c) $C_1$-$C_6$ straight or $C_1$-$C_9$ branched chain hydroxyalkyl;

and in addition $R_1$ and $R_2$ can be cyclohexyl;

wherein said amount is effective in inhibiting immune response by inhibiting the activity of IL-1, TNF, or other leukocyte derived cytokines on monocytes.

30. A method of inhibiting immune response in a mammal, wherein the method comprises administering to the mammal an amount of at least one xanthine of the formula:

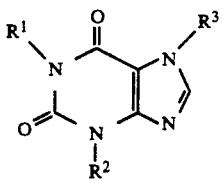

(II)

wherein $R_1$ and $R_2$ and $R_3$ are the same or different and are selected from the group consisting of (a) $C_1$-$C_6$ straight or branched chain alkyl;

(b) $C_1$-$C_6$ straight or branched chain alkoxyalkyl;

(c) $C_1$-$C_6$ straight or $C_1$-$C_9$ branched chain hydroxyalkyl;

and in addition $R_1$ and $R_2$ can be cyclohexyl;

wherein said amount is effective in inhibiting immune response by inhibiting the activity of IL-1, TNF, or other leukocyte derived cytokines on macrophages.

31. A method of inhibiting immune response in a mammal, wherein the method comprises administering to the mammal an amount of at least one xanthine of the formula:

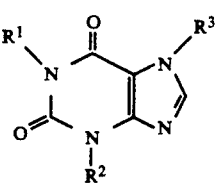

(II)

wherein $R_1$ and $R_2$ and $R_3$ are the same or different and are selected from the group consisting of (a) $C_1$-$C_6$ straight or branched chain alkyl;

(b) $C_1$-$C_6$ straight or branched chain alkoxyalkyl;

(c) $C_1$-$C_6$ straight or $C_1$-$C_9$ branched chain hydroxyalkyl;

and in addition $R_1$ and $R_2$ can be cyclohexyl;

wherein said amount is effective in inhibiting immune response by inhibiting the activity of IL-1, TNF, or other leukocyte derived cytokines on lymphocytes.

32. A method of alleviating an adverse condition in a mammal mediated by IL-1, TNF, or other leukocyte derived cytokines, which comprises administering to the mammal an amount of at least one xanthine of the formula:

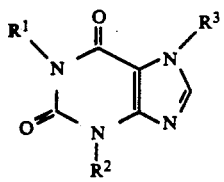
(II)

wherein $R_1$ and $R_2$ and $R_3$ are the same or different and are selected from the group consisting of
(a) $C_1$-$C_6$ straight or branched chain alkyl;
(b) $C_1$-$C_6$ straight or branched chain alkoxyalkyl;
(c) $C_1$-$C_6$ straight or $C_1$-$C_9$ branched chain hydroxyalkyl;
and in addition $R_1$ and $R_2$ can be cyclohexyl;
wherein said amount is effective in alleviating the activity, which mediates the adverse condition, of IL-1, TNF, or other leukocyte derived cytokines.

33. The method as claimed in any one of claims 26–32, wherein $R_1$ is a hydroxyalkyl radical.

34. The method as claimed in claim 33, wherein $R_2$ is a straight-chain or branched alkyl radical with 1 to 6 carbon atoms.

35. The method as claimed in claim 34, wherein the $R_3$ group stands for an aliphatic hydrocarbon group $R_5$ with up to 6 carbon atoms.

* * * * *